(12) United States Patent
Yang et al.

(10) Patent No.: US 11,311,569 B2
(45) Date of Patent: *Apr. 26, 2022

(54) ANTI-INFLAMMATORY COMPOSITION FOR IMPROVING INTESTINAL NUTRITIONAL METABOLISM FUNCTIONS AND INTESTINAL MICROECOLOGY, FOOD CONTAINING SAME, AND APPLICATION THEREOF

(71) Applicant: BEIJING RUIQIANJING SCIENCE AND TECHNOLOGY DEVELOPMENT CO. LTD., Beijing (CN)

(72) Inventors: Bingjun Yang, Beijing (CN); Mingguo Chi, Beijing (CN); Wei Bi, Beijing (CN)

(73) Assignee: BEIJING RUIQIANJING SCIENCE AND TECHNOLOGY DEVELOPMENT CO. LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/615,829

(22) PCT Filed: May 22, 2018

(86) PCT No.: PCT/CN2018/087763
§ 371 (c)(1),
(2) Date: Dec. 19, 2019

(87) PCT Pub. No.: WO2018/214855
PCT Pub. Date: Nov. 29, 2018

(65) Prior Publication Data
US 2020/0171074 A1    Jun. 4, 2020

(30) Foreign Application Priority Data
May 23, 2017  (CN) .......................... 201710367848.1

(51) Int. Cl.
| | | |
|---|---|---|
| A61K 31/733 | (2006.01) | |
| A23L 33/24 | (2016.01) | |
| A23L 33/26 | (2016.01) | |
| A61K 31/702 | (2006.01) | |
| A61K 31/717 | (2006.01) | |
| A61K 31/716 | (2006.01) | |
| A23L 33/21 | (2016.01) | |
| A23L 7/10 | (2016.01) | |
| A23L 29/244 | (2016.01) | |
| A61P 9/00 | (2006.01) | |

(Continued)

(52) U.S. Cl.
CPC .............. *A61K 31/733* (2013.01); *A21D 2/36* (2013.01); *A21D 13/062* (2013.01); *A23L 7/10* (2016.08); *A23L 7/109* (2016.08); *A23L 7/143* (2016.08); *A23L 7/198* (2016.08); *A23L 29/244* (2016.08); *A23L 33/125* (2016.08); *A23L 33/21* (2016.08); *A23L 33/24* (2016.08); *A23L 33/26* (2016.08); *A61K 31/702* (2013.01); *A61K 31/716* (2013.01); *A61K 31/717* (2013.01); *A61P 1/00* (2018.01); *A61P 3/00* (2018.01); *A61P 3/06* (2018.01); *A61P 3/10* (2018.01); *A61P 9/00* (2018.01); *A61P 19/06* (2018.01); *A61P 29/00* (2018.01); *A23P 30/20* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 2005/0271643 A1* | 12/2005 | Sorokulova | ............... A61P 1/00 424/93.462 |
| 2010/0047320 A1* | 2/2010 | Prakash | .................... A61P 3/00 424/439 |

(Continued)

FOREIGN PATENT DOCUMENTS

| | | |
|---|---|---|
| CN | 1423528 A | 6/2003 |
| CN | 101179954 A | 5/2008 |

(Continued)

OTHER PUBLICATIONS

English machine translation of ON 101537020, downloaded from translationportal.epo.org (Year: 2009).*

(Continued)

*Primary Examiner* — Eric Olson
(74) *Attorney, Agent, or Firm* — Bayramoglu Law Offices LLC

(57) ABSTRACT

An anti-inflammatory combination for improving nutrient metabolisms, intestinal functions and intestinal microecology and an anti-inflammatory food containing the anti-inflammatory combination are disclosed. The anti-inflammatory combination includes inulin, galacto-oligosaccharide, polydextrose, and a water-insoluble dietary fiber. Furthermore, a weight ratio of inulin, galacto-oligosaccharide, polydextrose and water-insoluble dietary fiber is 10-30:5-30:10-40:10-50. The anti-inflammatory food includes cereal flour, and the ratio of the cereal flour to the anti-inflammatory combination is 65-95:35-5. The anti-inflammatory combination is capable of reducing intestinal permeability, blood endotoxins, heavy metals and inflammatory factors, enhancing immunity, improving intestinal microecology and body biochemical indicators, and preventing chronic diseases.

22 Claims, 27 Drawing Sheets

(51) Int. Cl.

| | | |
|---|---|---|
| A61P 3/10 | (2006.01) | |
| A61P 1/00 | (2006.01) | |
| A23L 33/125 | (2016.01) | |
| A23L 7/143 | (2016.01) | |
| A23L 7/109 | (2016.01) | |
| A21D 2/36 | (2006.01) | |
| A21D 13/062 | (2017.01) | |
| A61P 19/06 | (2006.01) | |
| A61P 29/00 | (2006.01) | |
| A61P 3/00 | (2006.01) | |
| A61P 3/06 | (2006.01) | |
| A23P 30/20 | (2016.01) | |

(56) References Cited

U.S. PATENT DOCUMENTS

| | | | | |
|---|---|---|---|---|
| 2012/0027737 | A1* | 2/2012 | Leser | A23L 33/135 424/93.45 |
| 2020/0078391 | A1* | 3/2020 | Yang | A23L 7/10 |

FOREIGN PATENT DOCUMENTS

| | | | | |
|---|---|---|---|---|
| CN | 101268830 A | | 9/2008 | |
| CN | 101537020 A | | 9/2009 | |
| CN | 101766226 A | | 7/2010 | |
| CN | 102511713 A | | 6/2012 | |
| CN | 102987383 A | | 3/2013 | |
| CN | 103333840 A | | 10/2013 | |
| CN | 104171803 A | | 12/2014 | |
| CN | 106360310 A | * | 2/2017 | |
| CN | 106616998 A | | 5/2017 | |
| CN | 107198250 A | | 9/2017 | |
| WO | WO2012/027214 | * | 3/2012 | A23L 33/21 |

OTHER PUBLICATIONS

Dai et al., "Amino acid metabolism in intestinal bacteria: links between gut ecology and host health" Frontiers in Bioscience vol. 16 pp. 1768-1786 (Year: 2011).*

Slavin, J., "Fiber and Prebiotics: Mechanisms and Health Benefits" Nutrients vol. 5 pp. 1417-1435 (Year: 2013).*

Verbrugghe et al., "Oligofructose and inulin modulate glucose and amino acid metabolism through propionate production in normal-weight and obese cats" British Journal of Nutrition vol. 102 pp. 694-702 (Year: 2009).*

Janeiro et al., "Implication of Tri methylamine N-Oxide (TMAO) in Disease: Potential Biomarker or New Therapeutic Target" Nutrients vol. 10 p. 1398 (Year: 2018).*

Velazquez et al., "Trimethylamine N-Oxide: The Good, the Bad and the Unknown" Toxins vol. 8 p. 326 (Year: 2016).*

Rios-Covian et al., "IntestinalShortChainFattyAcidsandtheirLinkwithDietandHumanHealth" Fronteirs in Microbiology vol. 7 article 185 (Year: 2016).*

Fukodome et al., "Diamine oxidase as a marker of intestinal mucosal injury and the effect of soluble dietary fiber on gastrointestinal tract toxicity after intravenous 5-fluorouracil treatment in rats" Med Mol Morphol vol. 47 pp. 100-107 (Year: 2014).*

Hanzawa et al., "Clinical Significance of Serum Diamine Oxidase Activity in Inflammatory Bowel Disease: Importance of Evaluation of Small Intestinal Permeability" Inflamm Bowel Dis vol. 17 No. 2 p. E23 (Year: 2011).*

Rodriguez-Cabezas et al., "The combination of fructooligosaccharides and resistant starch shows prebiotic additive effects in rats" Clinical Nutrition vol. 29 pp. 832-839 (Year: 2010).*

Reddy et al., "Biochemical Epidemiology of Colon Cancer: Effect of Types of Dietary Fiber on Fecal Mutagens, Acid, and Neutral Sterols in Healthy Subjects" Cancer Research vol. 49 pp. 4629-4635 (Year: 1989).*

Jacobs et al., "Food Synergy: The Key to Balancing the Nutrition Research Effort" Public Health Reviews vol. 33 No. 2 pp. 507-529 (Year: 2011).*

Neustadt, J. "Western Diet and Inflammation" Integrative Medicine vol. 5 No. 4 pp. 14-18 (Year: 2006).*

Fuller et al., "New Horizons for the Study of Dietary Fiber and Health: A Review" Plant Foods Hum Nutr vol. 71 pp. 1-12 (Year: 2016).*

Lattimer et al., "Effects of Dietary Fiber and Its Components on Metabolic Health" Nutrients vol. 2 pp. 1266-1289 (Year: 2010).*

Zeng et al., "Mechanisms linking dietary fiber, gut microbiota and colon cancer prevention" World Journal of Gastrointestinal Oncology vol. 6 No. 2 pp. 41-51 (Year: 2014).*

Ackerman et al., "Infant food applications of complex carbohydrates: Structure, synthesis, and function" Carbohydrate Research vol. 437 pp. 16-27 (Year: 2016).*

Stevenson et al., "Wheat bran: its composition and benefits to health, a European perspective" International Journal of Food Science and Nutrition vol. 63 vol. 8 pp. 1002-1013 (Year: 2012).*

Wang et al., "Metabolite profiles and the risk of developing diabetes" Nature Medicine vol. 17 No. 4 pp. 448-454 (Year: 2011).*

Zhai et al., "Modulation of the gut microbiota by a galactooligosaccharide protects against heavy metal lead accumulation in mice" Food Funct vol. 10 pp. 3768-3781 (Year: 2019).*

Yamada et al., "Effect of Dietary Fiber on the Lipid Metabolism and Immune Function of Aged Sprague-Dawley Rats" Bioscience, Biotechnology, and Biochemistry vol. 67 No. 2 pp. 429-433 (Year: 2003).*

Faranghi et al., "The effect of enriched chicory inulin on liver enzymes, calcium homeostasis and hematological parameters in patients with type 2 diabetes mellitus: A randomized placebo-controlled trial" Primary Care Diabetes vol. 10 pp. 265-271 (Year: 2016).*

Hoeflinger et al., "Characterization of the Intestinal Lactobacilli Community following Galactooligosaccharides and Polydextrose Supplementation in the Neonatal Piglet" PLOS ONE 10(8) pp. 1-21, DOI: 10.1371/journal.pone.0135494 (Year: 2015).*

English machine translation of CN 106360310A, downloaded form translationportal.epo.org (Year: 2017).*

* cited by examiner

ANTI-INFLAMMATORY COMPOSITION FOR IMPROVING INTESTINAL NUTRITIONAL METABOLISM FUNCTIONS AND INTESTINAL MICROECOLOGY, FOOD CONTAINING SAME, AND APPLICATION THEREOF

CROSS REFERENCE TO THE RELATED APPLICATIONS

This application is the national phase entry of International Application No. PCT/CN2018/087763, filed on May 22, 2018, which is based upon and claims priority to Chinese Patent Application No. 201710367848.1, filed on May 23, 2017, the entire contents of which are incorporated herein by reference.

TECHNICAL FIELD

The present invention relates to the technical fields of improving low-grade chronic inflammatory response, immune decline, and metabolic block caused by the superposition effect of increased intestinal permeability, degradation of intestinal microbial diversity and intestinal microbial imbalance, preventing chronic diseases further induced thereby, and anti-inflammatory food. More specifically, the present invention relates to an anti-inflammatory combination for improving nutrient metabolism, intestinal functions, intestinal microecology, food, and the application thereof.

BACKGROUND

Since World War II, communicable diseases and infectious diseases have been controlled by vaccines and antibiotics. Chronic diseases have contributed to over 80% of human deaths. The causes of chronic diseases include enterogenic theory, lifestyle theory and other related theories and concepts. The enterogenic theory suggests that chronic diseases are induced by superposition of increased inflammatory factors in blood, metabolic disorders and immune dysfunction. These are caused by the destruction of intestinal barriers due to changes in food intake, chemical substances and antibiotics. In other words, the occurrence of enterogenic chronic diseases can be effectively prevented by improving intestinal barrier function.

The intestinal barriers are classified into biological barrier, chemical barrier, mechanical barrier and immune barrier. Among them, the chemical barrier is formed by a variety of chemical substances secreted by glands in the gastrointestinal tract. It is difficult to detect and perform target interventions without injury to the gastrointestinal tract. The mechanical barrier is characterized by the thickness of intestinal mucus, the number of goblet cells, the length of intestinal villi, the depth of fossae, the intestinal permeability, along with other measurements of the barrier. Among them, the intestinal permeability is very convenient to measure, which can facilitate the detection, research and development of intervention products. The immune barrier is similar to the mechanical barrier, where the improvement effect can also be easily monitored by measuring blood immune parameters. The biological barrier is the microbial diversity in the intestine. There are no widely accepted health standards of intestinal microecology thus far. It is generally believed that as the intestinal microbe diversity increases, the lactic acid-producing bacteria increases, the amount of short-chain fatty acids production increases, and the intestinal tract becomes healthier as a result of these changes. The necessary correlation between intestinal microorganisms and human health and the necessary correlation between intestinal microorganisms and diseases have been continuously confirmed, although there is no recognized disease-causing factor that is sufficient to cause disease other than pathogenic microorganisms. However, when the intestinal mechanical barrier is destroyed, the intestinal permeability increases. At this time, if the intestinal microecology deterioration occurs, the superposition effect will be generated, resulting in the increase of inflammatory factors in blood, immune disorders, and metabolic blocks or disorders. Therefore, the intestinal mechanical barrier destruction has been recognized as a sufficient factor to induce chronic diseases.

Regarding anti-inflammation and immunities, the body's immune balance is essential in maintaining good human health. Currently, people are often in a "sub-health state", and their immune systems may show dysfunction due to being constantly subjected to various stresses, resulting in an inflammatory response. This inflammatory response lies between the basal homeostatic state and the classic inflammatory response and is known as a low-grade chronic inflammation or para-inflammation (Medzhitov 2008). Cytokines are small molecule proteins with broad biological activity that are synthesized and secreted by immune cells or some non-immune cells due to external stimulations. The cytokines mainly include interleukins (IL), tumor necrosis factors (TNF), interferons (IFN), chemokines, colony stimulating factors (CSF), and any other equivalent. These cytokines can be used as biomarkers for the diagnosis of inflammations or diseases. Reducing inflammatory factors, increasing anti-inflammatory factors, and improving chemokines are important requirements for reducing inflammations and protecting physical health.

There are many well-known conclusions about the relationship between nutrient metabolisms and diseases. A team of scientists led by Thomas J. Wang, M.D, and Robert E. Gaston, M.D of Massachusetts General Hospital in the United States, followed up with 2,422 individuals having normal blood glucose for 12 years to study glucose and lipid metabolisms. The scientists ultimately discovered that 201 individuals developed diabetes. Amino acids, amines and other metabolites were analyzed in specific samples by liquid chromatography-tandem mass spectrometry. Five amino acids, including branched-chain amino acids and aromatic amino acids, i.e., isoleucine, leucine, valine, tyrosine and phenylalanine, were found to have a highly significant correlation with future diabetes. This result was reproduced in an independent prospective cohort study. These findings highlight the potential importance of amino acid metabolism in the pathogenesis of diabetes and contribute to the assessment and prevention of diabetic risks.

Regarding intestinal microbiota, current research suggests that the human body is a "super-organism" composed of human cells and all symbiotic microorganisms, which is a highly complex ecosystem. The number of microbial cells living inside and outside a human body is even 10 times that of the human body's own cells, which is made up with as much as hundreds of trillions of cells. Bacteria inhabits the adult intestine in the order of approximately $10^{14}$, which mainly colonize in the colon, forming an ecosystem with about 1.5 kg of microflora that includes 1,000 to 1,150 species of bacteria.

Nowadays, there is an opinion that numerous health problems of the human body are caused by the imbalance of microflora in the body, and the microecological balance is the determining factor. For example, intestinal flora is related to obesity, and the mechanism of the obesity caused by the intestinal microbial imbalance that mainly includes the following three aspects. First, some butyric acid-producing bacteria can degrade the polysaccharide in food into short-chain fatty acids for absorption and utilization by the body, thus improving the host's ability of absorbing energy from food. Second, the intestinal flora can further regulate the expression activity of energy storage tissue genes, and the genes mainly related to adipogenesis that includes fasting-induced adipose factor (Fiaf) and carbohydrate response element-binding protein (ChREBP)/sterol regulatory element-binding protein 1 (SREBP-1). Third, high-fat diets cause metabolic endotoxemia by changing the structure of intestinal flora, and then induce chronic systemic inflammations through the lipopolysaccharide (LPS)/cluster of differentiation 14 (CD14) signaling pathway, resulting in obesity, insulin resistance, among other metabolic changes. Further, other studies have shown that the metabolites of intestinal flora are associated with the increased incidence of major cardiovascular adverse events, and the intestinal flora is also associated with colorectal cancer. Moreover, there is another viewpoint that the toxin produced by the intestinal flora is an important cause of human aging and illness.

Based on people's new understanding of intestinal flora, the intestinal flora is an important factor in the pathogenesis of various chronic diseases. Currently, it has been reported that the regulation of the structure of intestinal flora can affect the synthesis and secretion of various gastrointestinal hormones. For instance, metabolic endotoxemia can be improved by increasing the concentrations of glucagon-like peptide-1 (GLP-1), glucagon-like peptide-2 (GLP-2) and decreasing the concentration of dipeptidyl peptidase IV (DDP-4) in the colon. Glycosidase inhibitors can significantly increase the number of probiotics such as bifidobacteria, improve glucose metabolism, and reduce adipose tissue inflammation.

After World War II, the nutritional food structure of most countries gradually changed. Since the twenty-first century, human beings have been faced with the enormous challenge of the "dietary fiber gap." The "dietary fiber gap" refers to the fact that in the modern day diet, it is difficult for people to eat enough dietary fiber according to the recommended standards. The body is in a low-grade inflammatory state for an extended amount of time, and the immunity is reduced, thereby causing various chronic diseases.

However, numerous problems still exist in the current research and application. 1) The enormous challenge of "dietary fiber gap" faced by human beings in the twenty-first century has not been solved. The nutrient metabolism is blocked and the intestinal microecology is destroyed, which causes the superposition effect. This problem induces the occurrence of various chronic diseases, and in turn makes chronic diseases account for more than 80% of human deaths, which is on the increase rather than the decrease. 2) There is no effective anti-inflammatory combination for simultaneously improving nutrient metabolisms, intestinal functions and intestinal flora imbalance. A single addition of the edible functional oligosaccharide combination or common oligosaccharide combination can produce positive effects on the human body. It will also cause the negative effects such as increased intestinal permeability, excess or insufficiency of individual beneficial bacteria, and equivalent negative effects. 3) There is a lack of research and applications of the synergistic effect of composite fibers to compensate for the drawbacks and deficiencies of simple oligosaccharide combinations. The supplementation of probiotics has a target defect of targeting the large intestine, and the supplementation of probiotic combinations also has the risk of increasing intestinal osmotic pressure and causing flora imbalance. 4) The difficulty of food selection is an important obstacle and hinder food balance. There is no effective and simple anti-inflammatory staple food for facilitating primary prevention and fundamentally prolonging the healthy life of human beings rather than relying on secondary prevention and clinical medicine to prolong the lifespan of human beings.

In summary, in recent years, associative analysis techniques, such as metabolomics, proteomics, metagenomics, immunohistochemistry and microbiology, have been gradually applied in the research of life sciences to study and develop anti-inflammatory combinations for improving nutrient deficient metabolisms, intestinal functions and intestinal microecology. Thereby eliminating pathogenic factors causing chronic inflammations and low immunity, among other equivalent deficiencies, improves the body's sub-health and prevent chronic diseases. It is an important nutritional health issue to develop anti-inflammatory foods simultaneously meeting human health needs and maintaining the intestinal micro-ecology. Based on this, the present invention develops an anti-inflammatory combination along with an anti-inflammatory food for improving nutrient metabolisms, intestinal functions, intestinal microecology, and further studies and expands the application field.

The present invention makes it very convenient to improve the human body's sub-health and effectively prevent chronic diseases. This invention is currently one of the most important research and development topics in human health today.

SUMMARY

The first technical problem to be solved by the present invention is to provide an anti-inflammatory combination for improving nutrient metabolisms, intestinal functions and intestinal microecology. The nutritional imbalance of modern fine-processed foods is improved, the rate of nutrient absorption is changed, the short-chain fatty acids increase, the nutrient metabolisms of branched-chain amino acids are enhanced, and the intestinal permeability, blood heavy metals, endotoxin and inflammatory factors are reduced. The environmental substances and nutrients for the survival of intestinal microbes are supplemented, thereby maintaining the homeostasis balance of intestinal microorganisms, and eliminating the pathogenic factors causing chronic inflammation, low immunity, among other pathogenic factors.

In order to solve the above technical problems, the present invention provides an anti-inflammatory combination for promoting nutrient metabolisms, reducing intestinal permeability and improving intestinal microecology. The anti-inflammatory combination includes inulin, galactooligo saccharides, polydextrose and water-insoluble dietary fiber, wherein, a weight ratio of the inulin, the galactooligosaccharides, the polydextrose and the water-insoluble dietary fiber is 10-30:5-30:10-40:10-50.

In a further improvement the inulin is oligofructose, polyfructose or a mixture of the oligofructose and the polyfructose; the water-insoluble dietary fiber is water-insoluble cellulose, hemicellulose, lignin or a mixture thereof.

The present invention further provides an anti-inflammatory food containing the above-mentioned anti-inflammatory combination. The anti-inflammatory food further includes a cereal flour, and the ratio of the cereal flour to the anti-inflammatory combination is 65-95: 35-5.

In a further improvement the ratio of the cereal flour to the anti-inflammatory combination is 75-90:25-10.

In a further improvement the cereal flour is a combination of one or more selected from the group consisting of wheat flour, rice flour, corn flour and whole potato flour. The anti-inflammatory food is prepared in a form of anti-inflammatory rice, anti-inflammatory flour, anti-inflammatory noodles, anti-inflammatory pasta, anti-inflammatory rice noodles, anti-inflammatory bread, anti-inflammatory bread dough and anti-inflammatory bread mix.

In a further improvement, a method for preparing the anti-inflammatory rice includes: mixing the cereal flour with the anti-inflammatory combination and extruding into a shape of rice by an extruding process, wherein, the water-insoluble dietary cellulose in the anti-inflammatory combination is microcrystalline cellulose.

The present invention further discloses an application of the above-mentioned anti-inflammatory combinations in preparation of food or a medicament for inhibiting inflammatory responses. This is characterized by using the anti-inflammatory combination, the inflammatory cytokines including interleukin-12p70 (IL-12p70), interleukin-13 (IL-13), interleukin-2 (IL-2), interleukin-23 (IL-23) and cytokine RANTES (regulated upon activation, normal T cell expressed and secreted) are reduced, and the anti-inflammatory cytokines, including interleukin-1 receptor antagonist (IL-1RA) and interleukin-4 (IL-4), are increased.

The present invention further discloses an application of the above-mentioned anti-inflammatory combination in a preparation of food or medicament for improving the utilization rate of glutamine, reducing the intestinal permeability targeting markers including D-lactic acid and diamine oxidase (DAO) in blood, improving intestinal functions and preventing inflammatory intestinal diseases.

The present invention further discloses an application of the above-mentioned anti-inflammatory combination in preparation of food or a medicament for increasing a production of short-chain fatty acids of intestinal microorganisms, lowering intestinal pH value, improving gastrointestinal motility and preventing constipation.

The present invention further discloses an application of the above-mentioned anti-inflammatory combination in preparation of food or a medicament for improving the metabolism of five amino acids composed of branched-chain amino acids and aromatic amino acids, i.e., leucine, isoleucine, valine, tyrosine and phenylalanine, significantly related to diabetes, and improving protein metabolism.

The present invention further discloses an application of the above-mentioned anti-inflammatory combination in preparation of food or a medicament for reducing intestinal permeability, inhibiting inflammatory response, boosting blood insulin, improving pancreatic function and protein metabolism, increasing blood insulin and preventing diabetes.

The present invention further discloses an application of the above-mentioned anti-inflammatory combination in preparation of food or a medicament for lowering low-density lipoprotein (LDL) cholesterol and triglyceride, improving lipid metabolism and preventing cardiovascular and cerebrovascular diseases.

The present invention further discloses an application of the above-mentioned anti-inflammatory combination in preparation of food or a medicament for reducing uric acid, improving nucleic acid metabolism, preventing gout and improving renal function.

The present invention further discloses an application of the above-mentioned anti-inflammatory combination in preparation of food or a medicament for reducing blood lead.

The present invention further discloses an application of the above-mentioned anti-inflammatory combination in preparation of food or a medicament for reducing alanine aminotransferase (ALT), indirect bilirubin, total bilirubin, and improving liver function.

The present invention further discloses an application of the above-mentioned anti-inflammatory combination in preparation of food or a medicament for improving hematological parameters of hemoglobin content, mean hemoglobin content, mean hemoglobin concentration and globulin, and strengthening sub-health physique.

The present invention further discloses an application of the above-mentioned anti-inflammatory combination in preparation of food or a medicament for improving albumin, albumin/globulin ratio (A/G) and immunoglobulin IgA, and improving immunocompetence.

The present invention further discloses an application of the above-mentioned anti-inflammatory combination in preparation of food or a medicament for improving intestinal microecology.

For such a design, the present invention has at least the following advantages.

In the anti-inflammatory combination of the present invention, through the reasonable combination containing the water-insoluble dietary fiber and the functional oligosaccharides, the release rate of nutrition in the intestine is adjusted, the digestion speed is slowed down, the cholesterol excretion is accelerated, the toxic substances in the food are absorbed and then excreted out of the body, especially the metabolism of branched chain amino acids and aromatic amino acids related to the prevention of diabetes is improved. The stability or decrease of biochemical indicators of blood trimethylamine-N-oxide (TMAO) is ensured, and the intestinal permeability is reduced. Meanwhile, the anti-inflammatory combination of the present invention has the function of water absorption and swelling, gradient bonding, mechanical isolation, mesh adsorption, ion exchange and microflora regulation, thus providing a favorable environment and foods for the growth of intestinal microorganisms, and maintaining the homeostasis balance of intestinal microorganisms. Through the synergistic effect of the anti-inflammatory combination, the negative effect of using the functional oligosaccharides alone is eliminated, the blood endotoxin, blood lead and inflammatory factors are reduced, the cell metabolism and body's immunity are enhanced, pathogenic factors causing chronic inflammations, low immunity and the like are eliminated, thereby effectively preventing the occurrence of chronic diseases such as cardiovascular and cerebrovascular diseases, such as diabetes among others. The combination of the present invention can effectively improve nutrient metabolisms, reduce intestinal permeability and maintain a homeostatic environment for intestinal microorganisms, and prevent chronic diseases.

The anti-inflammatory food containing the above-mentioned anti-inflammatory combination of the present invention, as an essential staple food for people every day, provides convenient balanced nutrients for the human body, thereby strengthening the physique, effectively preventing food-borne chronic diseases, and ensuring good health.

BRIEF DESCRIPTION OF THE DRAWINGS

The above summary is a description of the technical solutions of the present invention. For a clear understanding of the technical means of the present invention, the present invention is further described in detail below with reference to the accompanying drawings and specific embodiments.

FIGS. 11A-11F are first statistical scatter plots showing different results of data of blood biochemical indicators before and after 45 days of a feeding trial in all trial populations in Application Embodiment 2 of the present invention; wherein, FIG. 11A shows hemoglobin content data, FIG. 11B shows mean hemoglobin content data, FIG. 11C shows mean hemoglobin concentration data, FIG. 11D shows immune factor IgA data, FIG. 11E shows insulin data, and FIG. 11F shows triglyceride data.

FIGS. 12A-12F are second statistical scatter plots showing different results of data of blood biochemical indicators before and after 45 days of a feeding trial in all trial populations in Application Embodiment 2 of the present invention; wherein, FIG. 12A shows uric acid data, FIG. 12B shows serum lead content data, FIG. 12C shows albumin data, FIG. 12D shows globulin data, FIG. 12E shows albumin/globulin ratio data, and FIG. 12F shows alanine aminotransferase (ALT) data.

FIGS. 13A-13F are third statistical scatter plots showing different results of data of blood biochemical indicators before and after 45 days of a feeding trial in all trial populations in Application Embodiment 2 of the present invention; wherein, FIG. 13A shows total bilirubin data, FIG. 13B shows indirect bilirubin data, FIG. 13C shows high-density lipoprotein data, FIG. 13D shows low-density lipoprotein data, FIG. 13E shows D-lactic acid data, and FIG. 13F shows glutamine data.

FIGS. 14A-14F are first statistical scatter plots showing different results of data of amino acid indicators before and after 45 days of a feeding trial in all trial populations in Application Embodiment 2 of the present invention; wherein, FIG. 14A shows leucine data, FIG. 14B shows valine data, FIG. 14C shows phenylalanine data, FIG. 14D shows isoleucine data, FIG. 14E shows tyrosine data, and FIG. 14F shows sum of the foregoing five amino acid data.

FIGS. 15A and 15B are statistical scatter plots showing tyrosine and five amino acids data before and after 45 days of a feeding trial in each group of populations in Application Embodiment 2 of the present invention; wherein, FIG. 15A shows tyrosine data, and FIG. 15B shows sum of the foregoing five amino acids data.

FIGS. 16A and 16B are statistical scatter plots showing D-lactic acid and glutamine data before and after 45 days of a feeding trial in all trial populations in Application Embodiment 2 of the present invention; wherein, FIG. 16A shows D-lactic acid data and FIG. 16B shows glutamine data.

FIGS. 17A-17E are statistical scatter plots showing five descending cytokines data after 45 days of a feeding trial in all trial populations in Application Embodiment 2 of the present invention; wherein, FIG. 17A shows cytokine IL-12p70 data, FIG. 17B shows cytokine IL-13 data, FIG. 17C shows cytokine IL-2 data, FIG. 17D shows cytokine IL-23 data, and FIG. 17E shows cytokine RANTES data.

FIGS. 18A-18E are statistical scatter plots showing five rising cytokines data after 45 days of a feeding trial in all trial populations in Application Embodiment 2 of the present invention; wherein, FIG. 18A shows cytokine IL-IRA data, FIG. 18B shows cytokine interleukin-7 (IL-7) data, FIG. 18C shows cytokine tumor necrosis factor β (TNF-β) data, FIG. 18D shows cytokine monocyte chemoattractant protein-1 (MCP-1) data, and FIG. 18E shows cytokine macrophage inflammatory protein 1 α (MIP-1 α) data.

FIGS. 19A-19D are statistical scatter plots showing four rising cytokines data after 45 days of a feeding trial in all trial populations in Application Embodiment 2 of the present invention; wherein, FIG. 19A shows cytokine interferon-gamma-inducible protein 10 (IP-10) data, FIG. 19B shows cytokine tumor necrosis factor α (TNF-α) data, FIG. 19C shows cytokine granulocyte macrophage-colony stimulating factor (GM-CSF) data, and FIG. 19D shows cytokine interleukin-18 (IL-18) data.

FIGS. 20A-20D are statistical scatter plots showing four rising cytokines data after 45 days of a feeding trial in all trial populations in Application Embodiment 2 of the present invention; wherein, FIG. 20A shows cytokine interleukin-27 (IL-27) data, FIG. 20B shows cytokine interleukin-15 (IL-15) data, FIG. 20C shows cytokine IL-4 data, and FIG. 20D shows cytokine growth-related oncogene-α (GRO-α) data.

DETAILED DESCRIPTION OF THE EMBODIMENTS

Figure 1:
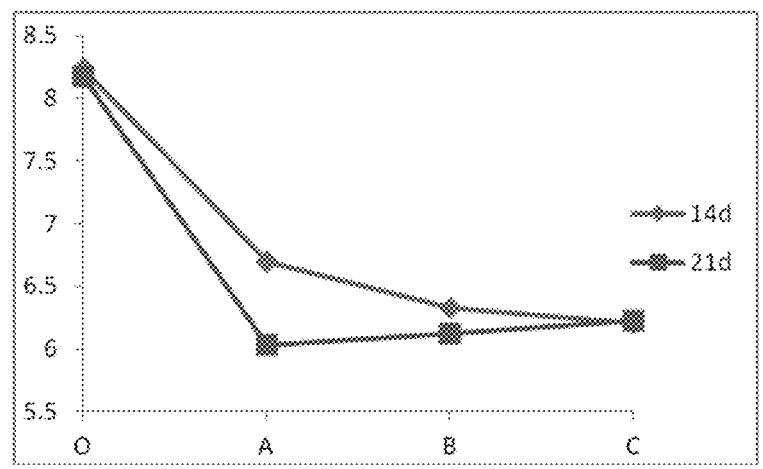
FIG. 1 is a diagram showing changes in the pH value of intestinal contents of mice in Application Embodiment 1 of the present invention.

According to the present invention, an anti-inflammatory combination for improving nutrient metabolisms, reducing intestinal permeability and improving intestinal microecology includes inulin, galactooligosaccharide, polydextrose and water-insoluble dietary fiber, wherein, a weight ratio of the inulin, the galactooligosaccharide, the polydextrose and the water insoluble dietary fiber is 10-30:5-30:10-40:10-50.

In the present invention, the inulin is an oligofructose, polyfructose or a mixture of oligofructose and polyfructose. The galactooligosaccharides (GOS) are functional oligosaccharides with natural properties, the molecular structure thereof is generally formed by linking 1-7 galactosyl groups to a galactose (Gal) or glucose (Glc) molecule, i.e., Gal-(Gal)n-Glc/Gal (n is 0-6). The polydextrose is a water-soluble dietary fiber. The water-insoluble dietary fiber is water-insoluble cellulose, hemicellulose, lignin or a mixture thereof; and regarding the particle size, microcrystalline cellulose may be used.

In order to allow the anti-inflammatory combination for improving nutrient metabolisms, reducing intestinal permeability and improving intestinal microecology to act easily on the human body, the present invention further provides an anti-inflammatory food containing the above-mentioned anti-inflammatory combination. The anti-inflammatory food further includes a cereal flour, and according to the present invention, the weight ratio of the cereal flour to the anti-inflammatory combination as a formula is 65-95:35-5.

Furthermore, the cereal flour is wheat flour, rice flour (japonica rice, indica rice, and glutinous rice), corn flour, whole potato flour or a combination thereof. The balanced anti-inflammatory food formed by the cereal flour and the above-mentioned combination mainly includes various forms of food such as anti-inflammatory rice, flour, noodles (hand-made noodles, dried noodles, semi-dried noodles, and wet noodles), pasta, rice noodles, bread, bread dough or bread mixes, and other forms of food that are not limited to these forms.

In the present invention, the preferred weight ratio of the cereal flour to the anti-inflammatory combination in the formula is 75-90: 25-10.

Obviously, the anti-inflammatory food of the present invention may further include minerals, vitamins, and nutritional enhancers and supplements such as xylo-oligosaccharide, L-arabinose, stachyose, guar gum, etc., and the addition range thereof is in accordance with the requirements of General Principles for the Addition of Essential Nutrients to Food of Codex Alimentarius Commission (CAC).

The anti-inflammatory combination of the present invention can improve nutrient metabolisms. The water-insoluble dietary fiber slows down the digestion speed and accelerates the excretion of cholesterol, endotoxins and heavy metals, maintains the living environment of intestinal microorganisms, and has functions such as water absorption to prevent swelling, gradient bonding, mechanical isolation, mesh adsorption, ion exchange and microflora regulation. In the present invention, each of the inulin, the galactooligosaccharide and the polydextrose can promote the growth and reproduction of beneficial bacteria and inhibit the growth and activity of harmful bacteria by selectively stimulating the growth and activity of one or several species of beneficial bacteria. The balanced anti-inflammatory food of the present invention is capable of maintaining the homeostatic environment of intestinal microorganisms well, reducing the intestinal permeability, eliminating the pathogenic factors causing chronic inflammations, immune disorders, and other pathogenic factors, effectively strengthening the physique, and preventing chronic diseases.

Product Embodiment 1: Anti-Inflammatory Nutritious Rice

The cereal flour is a rice flour mixture formed by mixing japonica rice flour and glutinous rice flour mixed with the weight ratio 80:20. The anti-inflammatory combination is a mixture formed by mixing inulin, galactooligosaccharide, polydextrose, and microcrystalline cellulose with the weight ratio of 30:10:30:30. And the weight ratio of the cereal flour to the anti-inflammatory combination is 85:15.

The method for preparing the anti-inflammatory nutritious rice is as follows.

1. The components of the anti-inflammatory combination are taken according to the ratio and mixed thoroughly with a blender to prepare a premixed powder material for subsequent use.

2. The japonica rice flour is mixed with the glutinous rice flour in the ratio of 80:20 to obtain a rice flour mixture. The rice flour mixture is mixed with the premixed powder material obtained in step 1 in the weight ratio of 85:15. Subsequently, 27% to 29% water is added, and then stirred and tempered to obtain a semi-finished product of the anti-inflammatory nutritious rice.

3. The semi-finished product of the anti-inflammatory nutritious rice obtained in step 2 is extruded and granulated by a twin-screw extruder, dried by a fluidized bed dryer, and then cooled and sieved to obtain the anti-inflammatory nutritious rice of this embodiment.

In this embodiment, the finished product of the anti-inflammatory nutritious rice is similar to natural rice shape with an attractive appearance. The taste of the finished product is delicate and smooth without any graininess or retrogradation. The finished product has the following functional characteristics: meeting the human body's anti-inflammatory nutrition requirements, glycemic indicator less than 50, and improving constipation and intestinal microecological environment.

Product Embodiment 2: Anti-Inflammatory Nutritious Flour

The cereal flour is a common flour. The anti-inflammatory combination is a mixture formed by mixing inulin, galactooligosaccharide, polydextrose, and microcrystalline cellulose in the weight ratio of 30:5:40:25. The weight ratio of the cereal flour to the anti-inflammatory combination is 80:20.

The method for preparing the anti-inflammatory nutritious flour is as follows.

1. The components of the anti-inflammatory combination are taken according to the ratio and mixed thoroughly with a blender to prepare a premixed powder material for subsequent use.

2. The common flour is mixed with the premixed powder material obtained in step 1 in the weight ratio of 80:20, then stirred, tempered fully, and sieved to obtain the anti-inflammatory nutritious flour of this embodiment.

In this embodiment, the finished product of the anti-inflammatory nutrient flour is similar to common flour in shape, has a fine taste without any graininess for all kinds of pasta. The finished product has the following functional characteristics: meeting the human body's anti-inflammatory nutrition requirements, glycemic indicator less than 50, and improving constipation and intestinal microecological environment.

Product Embodiment 3: Anti-Inflammatory Nutritious Noodles

The cereal flour is a common flour. The anti-inflammatory combination is a mixture formed by mixing an inulin, galactooligosaccharide, polydextrose, and microcrystalline cellulose in the weight ratio 10:30:10:50. The weight ratio of the cereal flour to the anti-inflammatory combination is 65:35.

The method for preparing the anti-inflammatory nutritious noodles is as follows.

1. The components of the anti-inflammatory combination are taken according to the ratio and mixed thoroughly with a blender to prepare a premixed powder material for subsequent use.

2. The common flour is mixed with the premixed powder material obtained in step 1 in the weight ratio of 65:35, added with water and stirred until the water content is about 45%. The water temperature is controlled to range from 15° C. to 20° C., and the stirring is performed for 10 to 15 minutes;

3. Ripening is performed for 10 to 15 minutes at a ripening temperature of about 25° C., followed by rolling, cutting, drying, shaping in cold air, and reducing the water content to 14% to obtain the anti-inflammatory nutritious noodles of this embodiment.

In this embodiment, the anti-inflammatory nutritious noodles have a delicate, smooth and chewy taste with the following functional characteristics: meeting the human body's anti-inflammatory nutrition requirements, glycemic indicator less than 50, and improving constipation and intestinal microecological environment.

Product Embodiment 4: Anti-Inflammatory Nutritious Bread

The grain flour is a medium-gluten flour. The anti-inflammatory combination is a mixture formed by mixing inulin, galactooligosaccharide, polydextrose, and microcrystalline cellulose in the weight ratio of 30:30:30:10. The weight ratio of the cereal flour to the anti-inflammatory combination is 95:5.

The method for preparing the anti-inflammatory nutritious bread is as follows

1. The components of the anti-inflammatory combination are taken according to the ratio and mixed thoroughly with a blender to prepare a premixed powder material for subsequent use combination.

2. The medium-gluten flour is mixed with the premixed powder material obtained in the step 1 in the weight ratio of 95:5, then added with water and stirred. Then, according to a traditional bread process, dough kneading, first fermentation, second dough kneading, second fermentation, shaping, molding, pre-baking processing, baking and cooling are performed in order to obtain the anti-inflammatory nutritious bread bar of this embodiment. In this step, the ingredients, such as white granulated sugar, vegetable oil and other ingredients, used in the traditional bread production, are eliminated due to the characteristics of the components of the anti-inflammatory combination.

In this embodiment, the anti-inflammatory nutritious bread has a delicate and smooth taste, a fluffy and soft tissue, and a resistance against collapse with the following functional characteristics: meeting the human body's anti-inflammatory nutrition requirements, and improving constipation and intestinal microecological environment.

The anti-inflammatory combination of the present invention can improve nutrient metabolisms. The water-insoluble dietary fiber slows down the digestion speed and accelerates the excretion of cholesterol, endotoxin and heavy metals, maintains the living environment of the intestinal microorganisms, and has the functions of water absorption and reduction in swelling, gradient bonding, mechanical isolation, mesh adsorption, ion exchange and microflora regulation. In the present invention, the inulin, the galactooligosaccharides and the polydextrose can promote the growth and reproduction of beneficial bacteria and inhibit the growth and activity of harmful bacteria by selectively stimulating the growth and activity of one or several species of beneficial bacteria. The balanced anti-inflammatory food of the present invention is capable of maintaining the homeostatic environment of intestinal microorganisms well, reducing the intestinal permeability, eliminating the pathogenic factors causing chronic inflammations, immune disorders, among other pathogenic factors, effectively strengthening the physique, and preventing chronic diseases.

Application Embodiment 1

In this experiment, glycan combinations are classified into three types including 1) a combination of functional glycanscombination; 2) a combination of a common glycanscombination; and 3) a combination including a plurality of functional glycans and common glycans. The synergistic effect of different types of the glycan combinations is investigated. The synergistic effect mainly includes the following two aspects. First, changes of suitable microbial abundance and the microbial living environment. Second, changes of the effects on the host physiological indicators. The specific steps of the experiment are as follows.

1. Materials and Devices
1.1 Reagent
DAO kit, SCFA kit and TMAO kit, supplied by Shanghai Meilian Biotechnology Co., Ltd.
1.2 Experimental Animals
8-week-old specific pathogen-free (SPF) grade BARBL/C mice were purchased from the Experimental Animal Center of the Academy of Military Medical Sciences, China.
1.3 Experimental Feed
Four experimental feed groups were prepared according to the classification of the above-mentioned glycan combinations. Combination Blank group O: 100% base feed. Namely, the common feed for mice.

Experimental group A: base feed+combination of functional glycanscombination. Specifically: base feed 85%, galactogalactose 7.5%, and inulin 7.5%.

Experimental group B: base feed+combination of common glycanscombination. Specifically: base feed 85%, insoluble dietary fiber 7.5% (extracted from wheat bran), and polydextrose 7.5%.

Experimental group C: base feed+combination of functional glycans combination+combination of common glycanscombination. Specifically: base feed 85%, galactogalactose 4%, inulin 3.5%, insoluble dietary fiber 4%, and polydextrose 3.5%. The above-mentioned experimental feeds were all provided by Beijing Ruiqianjing Science and Technology Development Co., Ltd. Moreover, the above-mentioned formulas are to be made into food, the effect to be reached refers to 37-45 g of edible dietary fiber composite for 250-300 g of staple food per day.

1.4 Main Instruments and Devices
An electronic balance and a pH meter, provided by Mettler-Toledo Instruments (Shanghai) Co., Ltd; a gas chromatography mass spectrometer (GC-MS).
2. Experimental Methods
2.1 Experimental Design
The mice were randomly allocated into the blank group O, experimental group A, experimental group B, and experimental group C (8 mice/group) and were fed in an individually ventilated caging system where 12 h light/12 h night was strictly controlled and the ambient temperature was set to be 222e The experiment lasted 4 weeks, wherein the first week was the adaptation period, and the second, third and fourth weeks were the experimental period. During the adaptation period, all four groups of mice were fed with the blank feed (i.e. 100% base feed). During the experimental period, the mice of the blank group O were fed with the blank feed, and the mice of the experimental groups were fed with the corresponding feeds in the experimental group A, experimental group B, and experimental group C, respectively. At the end of the second week and at the end of the third week during the experimental period, 3 mice were randomly selected, blood was collected from the eyeball, the mice were sacrificed by dislocation, the small intestine was taken and stored in a formalin solution for hematoxylin-eosin (HE) staining. The colon content samples were collected and stored at −80° C. and the pH, bacterial flora composition and the like were analyzed. Serum was separated after collecting the blood. Various biochemical indicators such as diamine oxidase (DAO), trimethylamine oxide (TMAO) and short-chain fatty acid (SCFA) in the serum were measured by the kits.

2.2 Determination of Serum Metabolic Parameters

After the blood was collected from the mouse eyeballs, the blood was placed at room temperature for 1 h, then centrifuged at 3000 rpm for 15 min for separation to obtain a supernatant serum, and the supernatant serum was stored at −80° C. The biochemical indicators of the serum, including DAO, TMAO and SCFA, were determined by the kits.

2.3 Determination of pH of Intestinal Contents 100 mg of the intestinal contents was weighed, added with deionized water at 15 mL/g, sufficiently dispersed, and centrifuged at 13,000 g for 2 min, and then the pH of the supernatant was measured with the pH meter.

2.4 Determination of Metabolomics of Intestinal Contents 100 mg of the sample was weighed, added with a solution formed by methanol, water and chloroform in a weight ratio of 3:1:1, uniformly dispersed by vortex shaking, placed for 12 h, and centrifuged to obtain a supernatant. 100 μl of the extract was taken, added with 20 μL of 0.2 mg/mL ribitol as an internal standard substance, sufficiently mixed, and then dried by blowing $N_2$ at 45° C. 40 μL of 20 mg/mL methoxyamine hydrochloride solution was added to the dried extract, sufficiently mixed, and reacted at 130 rpm for 90 min at 30° C. After sufficient reaction, 40 μL of N, O-bis (trimethylsilyl) trifluoroacetamide (BSTFA) (containing 1% trimethylchlorosilane (TMCS)) was further added, sufficiently mixed, then maintained in a gas bath at 37° C. for 30 min, followed by taking out and placed at room temperature for 120 min, and then stored at 4° C. for subsequent determination.

GC-MS chromatographic conditions: Gas chromatography (GC) conditions: Agilent 7890, tandem LECO Pegasus 4D TOF/MS instrument;

Gerstel multipurpose sampler (MPS) injection system; chromatographic column: DB-5MS 30 m×250 μm×0.25 mm;

Temperature programming: 70° C., maintaining for 1 min, then rising to 280° C. at 5° C./min, and maintaining for 10 min;

Carrier gas was He; flow rate was 1 mL/min; injection volume was 1, then maintained in rnatantMass spectrometry (MS) conditions:

MS conditions: electron ionization (EI) source: mass scanning range: 50-800 Da, scanning speed: 10/s; temperatures at injection port, transmission line and ion source: 250° C., 250° C. and 220° C., respectively.

Data Processing

Each compound in the chromatogram was subjected to chromatographic peak alignment, deconvolution, and peak search by the workstation Chroma TOF software 4.50 version (identified by mass spectrometry databases such as its own National Institute of Standards and Technology (NIST) mass spectrometry database, and related standard substance). Then, the original chromatogram was normalized by ribitol (internal standard substance) and integrated (signal-to-noise ratio S/N>100) to finally obtain related data of each chromatographic peak, metabolite name and peak area.

2.5 Measurement of Changes in Villus Height and Fossae Depth in Small Intestine

Method of analyzing villus length, fossae depth, and goblet cells in intestinal tissue by Image pro-plus 6.0 (IPP): the villus length and the fossae depth of each slice were measured by using a line tool of the IPP software to select a picture having stretched villi and having complete intestine villi.

2.6 Determination of 16S DNA of Intestinal Contents

The extraction of microbial DNA was performed according to the instructions of the kit (Omega Bio-tek, Norcross, Ga., U.S.) for extracting the DNA of the intestinal contents. The mass of the extracted DNA was detected by 1% agarose gel electrophoresis. The DNA samples were stored in a −20° C. refrigerator. The polymerase chain reaction (PCR) amplification was performed for the 16S v3-v4 hypervariable regions of the bacterial 16S rRNA gene by high-throughput sequencing in the Illumina MiSeq sequencing platform PE300 (the amplification conditions: unwinding at 95 for the 16S v95Seq sequencing platform PE300PE300he bacterial 16S rRNA g300 (the amplification conditions: unwinding at 95° C. for 2 min, 3-v4 hypervariable regions of the bacterial 16S rRNA gene by high-throughput sequencing in the Illumina rksGTTT-3', and for each sample, an 8 bp tag sequence was added. Each sample was amplified in triplicate in a 25 μs reaction system including 2.5 μr of 10 onPyrobest Buffer, 2 encing platform PE300 (the amplification conditions: unwinding at 95 at 95nding at 95 ng at 9595Seq sequencing platform PE300PE300he bacterial 16S rRNA g300 (the amplifig in the Illumina rksGTning being ddH$_2$O. The amplicons were recovered by a 2% agarose gel, purified according to the instructions of the AxyPrep DNA Gel Extraction Kit (Axygen Biosciences, Union City, Calif., U.S.), and quantified by QuantiFluor™-ST (Promega, U.S.). The purified amplicons were mixed in equal amounts and were then subjected to double-ended 2×300 bp sequencing according to the standard protocol of the Illumina MiSeq sequencing platform. The original fastq file was processed by the QIIME (version 1.17) software according to the following processing criteria: (i) 10 bp was used as a sliding window. If the average mass value in the window is less than 20, then the back-end base is truncated from the window and the sequence of less than 50 bp is filtered out. (ii) The samples are distinguished according to the tag sequence. The mismatch number in the tag sequence was allowed to be 0. The mismatch number of the primers was allowed to be 2 and sequences containing the fuzzy bases were removed. (iii) Between the sequences spliced together, the overlap region should be equal to or more than 10 bp, and sequences that cannot be spliced were removed. UPARSE (version 7.1 http://drive5.com/uparse/) software was used to generate operational units (OTUs) with a similarity of 97% by clustering. Subsequently, the chimeric sequences were identified by UCHIME software and were removed. For taxonomic alignment, the Silva (SSU115) 16S rRNA database was used with an algorithm RDP Classifier (http://rdp.c-me.msu.edu/) and a confidence threshold of 70%.

3. Results and Conclusions 3.1 pH of Intestinal Contents

Referring to FIG. 1, the pH values of the intestinal contents of the mice in the blank group O were 8.23 and 8.17 on days 14 and 21, respectively. The pH values of the intestinal contents of the mice in the experimental groups A, B and C decreased sharply to about 6.0, and the values of the experimental group C were the most stable. This is because bacteria decomposes oligosaccharides and produce short-chain fatty acids, which lowers the pH values.

The intestinal pH value is an important parameter of intestinal microecology, and the pH values change significantly. From this experiment, it can be seen that the formula feed of the experimental group C is the most stable and ideal.

3.2 Serum Biochemical Indicators of Mice

TABLE 1

Changes in serum biochemical indicators of mice after intervention in the experimental feed groups

| | Indicator | | |
|---|---|---|---|
| Processing | SCFA (pg/mL) | TMAO (ng/mL) | DAO (U/L) |
| O-14 | 197.29 | 49.64 | 89.87 |
| A-14 | 189.75 | 62.77 | 58.33 |
| B-14 | 154.50 | 45.00 | 81.00 |
| C-14 | 145.88 | 38.38 | 76.93 |
| O-21 | 199.38 | 54.15 | 87.60 |
| A-21 | 225.62 | 79.92 | 100.67 |
| B-21 | 233.75 | 102.08 | 91.40 |
| C-21 | 196.13 | 51.31 | 70.87 |

Figure 2:
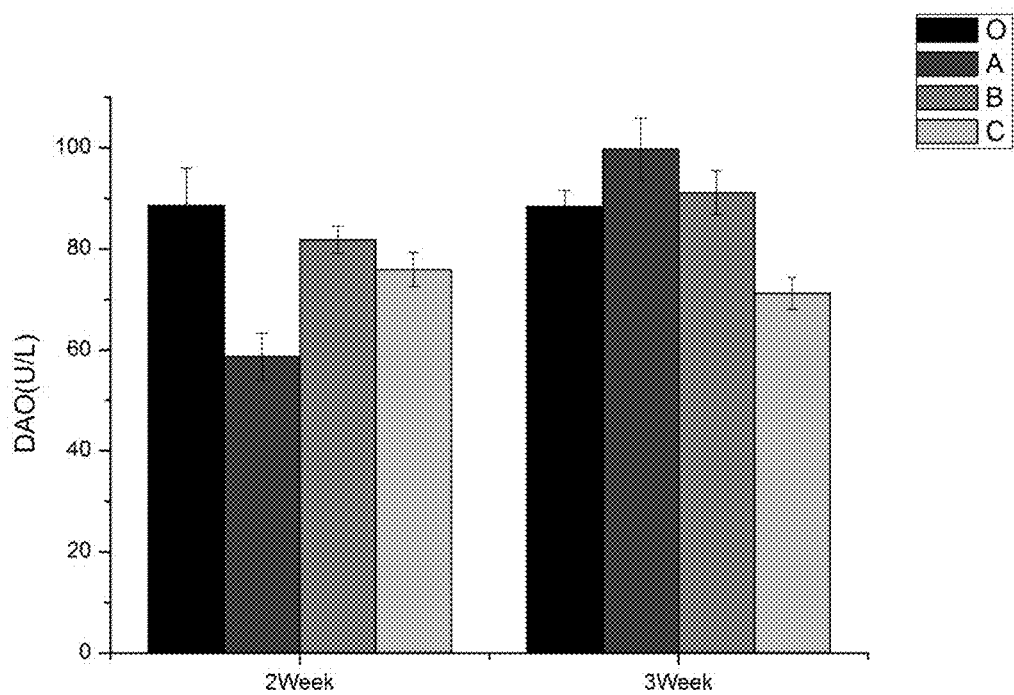
FIG. 2 is a diagram showing changes in serum biochemical indicator DAO of mice in Application Embodiment 1 of the present invention.
Figure 3:
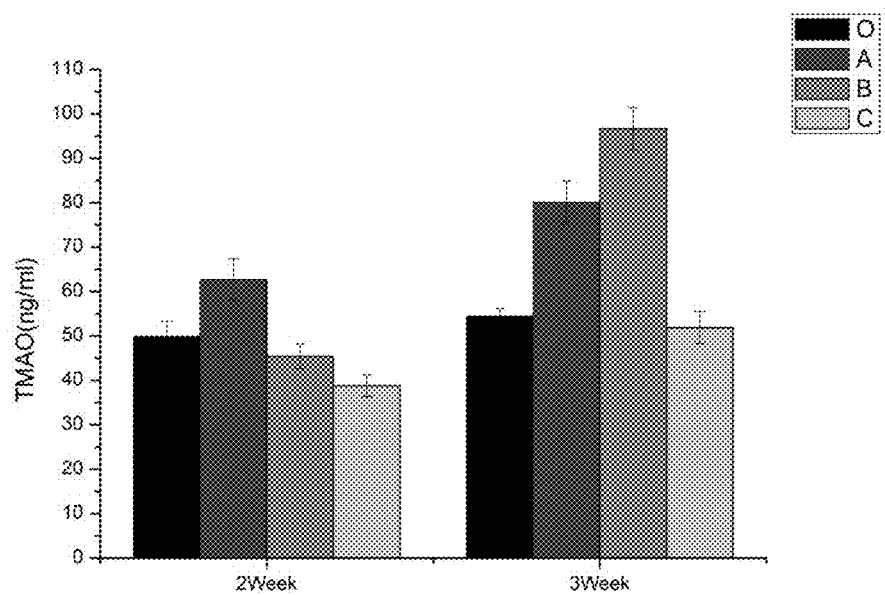
FIG. 3 is a diagram showing changes in serum biochemical indicator TMAO of mice in Application Embodiment 1 of the present invention.
Figure 4:
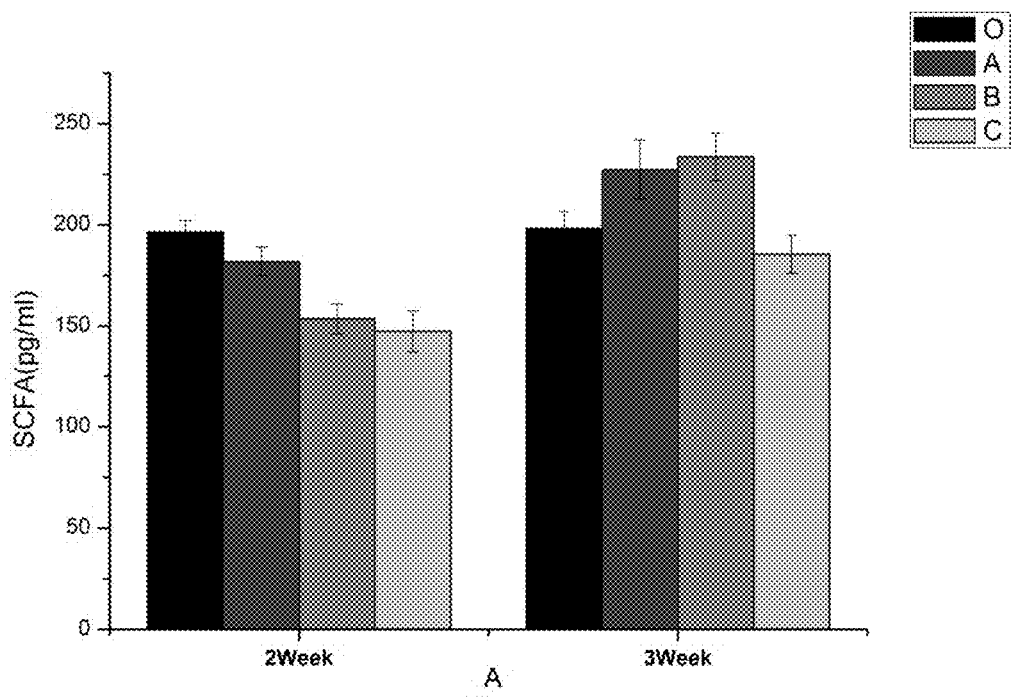
FIG. 4 is a diagram showing changes in serum biochemical indicator short chain fatty acid (SCFA) of mice in Application Embodiment 1 of the present invention.

It can be seen from Table 1 and FIGS. 2-4, the results of comparing each indicator of the serum of mice in the experimental groups with that in the blank group are as follows.

Experimental group A: the change of the DAO indicator is unstable, the TMAO value has a negative change (increase), and the change of the SCFA is not significant.

Experimental group B: the change of the DAO indicator is not significant, the negative change of the TMAO value at day twenty-one is large (increased), and the change of the SCFA is large.

Experimental group C: the change of the DAO indicator is significant, the change of the TMAO is significant, and the change of the SCFA is significant.

Since diamine oxidase (DAO) is an internal enzyme of intestinal mucosal cells, the level of the DAO in the blood directly expresses the degree of damage of the intestinal mucosa and the level of intestinal permeability. It is generally believed that oligosaccharides selectively promote the proliferation of probiotics in the intestine, thereby improving the health of the host. However, it has also been reported that oligofructose increases the permeability of the rat's intestine, and even increases the ectopic of *Salmonella* at high doses. Excessive consumption of oligosaccharides may also cause intestinal discomfort, such as borborygmus and flatulence. As can be seen from Table 1, at the end of the second week of the experimental period, the mice in the group A have the lowest DAO value, but the DAO value is increased at the end of the third week of the experimental period. The reasons may be that excessive combinations of functional oligosaccharides increase intestinal permeability in mice, resulting in an increase of the DAO value. However, the DAO value of the mice in the group C showed a gradually decreasing process, indicating that the synergistic effect of the formula of the group C made up for the important drawbacks of the formulas of the groups A and B, and the formula of the group C is an ideal formula combination.

Trimethylamine (TMAO), a choline metabolite that depends on intestinal microorganisms, plays an important role in the occurrence and development of cardiovascular diseases. The level of TMAO in the host shows obviously positive correlation with cardiovascular diseases. Intestinal microorganisms use the intake nutrients such as lecithin, choline, and carnitine as sources of carbon energy. Intestinal microorganisms have a trimethylamine lyase (the mammal does not have this enzyme), which can break the C—N bond of these nutrients, and then the trimethylamine is released as a metabolic waste, entered the liver through the portal vein, and is oxidized to form TMAO by the flavin monooxygenase, mainly flavin-containing monooxygenase 3 (FMO3), in the liver.

At the end of the second week and the third week of the experimental period, the values of the groups A and B were even higher than that of the blank group O, and a negative effect occurred, indicating that although the combination of the functional glycans and the combination of the common glycans have an influence on the intestinal micro-ecology, they have a negative effect on the host at stages. The TMAO value in the serum of the mice in the group C was the lowest, indicating that the feed of the group C can promote the growth of probiotics, balance the microbial steady state, and inhibit the microorganisms that can produce trimethylamine precursors.

Short-chain fatty acids (SCFA) play an important role in maintaining intestinal health in the human body. In particular, butyric acid, as a growth-inducing agent for colonic mucosa and an inhibitor of inflammation, can induce apoptosis of cancer cells and prevent colon cancer. The content of SCFA in the intestine can reflect the bacterial activity and affect the regulation of liver lipids and carbohydrates. The bacteria use oligosaccharides to produce short-chain fatty acids. Referring to FIG. 1, the pH values of the intestinal contents of the mice in the experimental groups A, B, and C were significantly lower than those in the blank group. However, from the analysis of the serum determination results in the second week of the experimental period, it was found that the SCFA in the serum of the mice in the blank group were the highest. At the end of the third week of the experimental period, the serum results showed that the change in the group C was not obvious. This result was related to the decrease of the permeability due to the thickening of the intestinal mucosal, which was consistent with the lowest DAO in the serum of the group C.

In summary, the feeds of the experimental groups A, B, C represent three types of formulas, where the formula of the group C is the most ideal type of formula. The synergistic effect of the components in the group C had a positive effect on the steady state balance of the intestinal micro-ecology and the host without causing side effects. The formulas of the groups A and B had a positive effect on the steady state balance of the intestinal micro-ecology and the host, but they both have certain side effects in some stages. This is further confirmed in the subsequent experimental results.

3.3 Effects on Villus Height and Fossae of Small Intestine

TABLE 2

Changes of villus height and fossae depth of small intestine after feed intervention in experimental groups

| | Indicator | | |
|---|---|---|---|
| Processing | Villus height (mm) | Fossae/Fossae depth (mm) | V/F |
| O-14 | 0.535 | 0.157 | 3.460 |
| A-14 | 0.494 | 0.133 | 3.791 |
| B-14 | 0.590 | 0.144 | 4.171 |
| C-14 | 0.462 | 0.145 | 3.278 |
| O-21 | 0.272 | 0.075 | 3.833 |
| A-21 | 0.349 | 0.112 | 3.113 |

TABLE 2-continued

Changes of villus height and fossae depth of small intestine after feed intervention in experimental groups

| Processing | Indicator | | |
|---|---|---|---|
| | Villus height (mm) | Fossae/Fossae depth (mm) | V/F |
| B-21 | 0.474 | 0.121 | 4.157 |
| C-21 | 0.584 | 0.130 | 4.757 |

Figure 5:
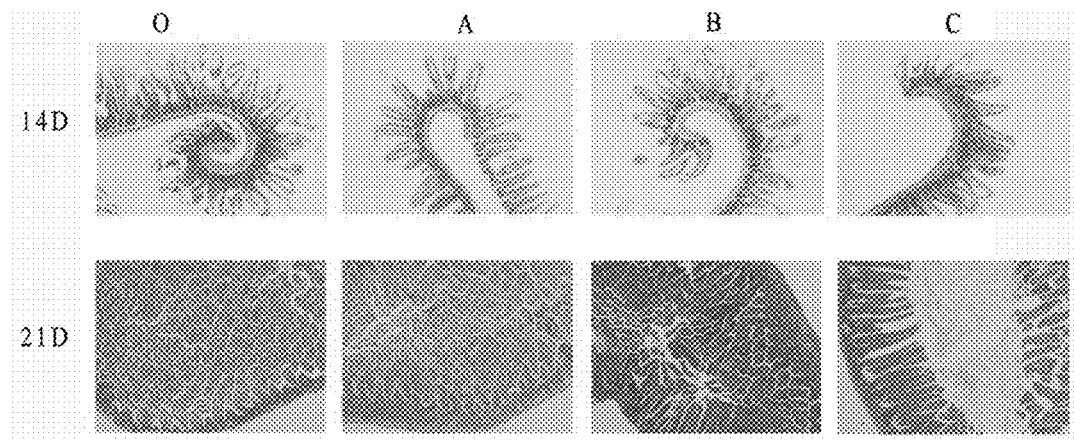
FIG. 5 is a diagram showing changes in villus height and fossae section of small intestine of mice in Application Embodiment 1 of the present invention.
Figure 6:
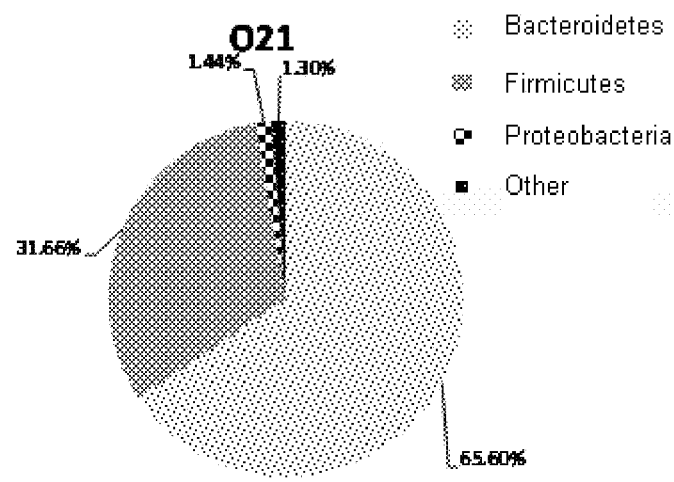
FIG. 6 is a diagram showing the composition of intestinal flora at a phylum level in mice of experimental group O at day 21 in Application Embodiment 1 of the present invention.
Figure 7:
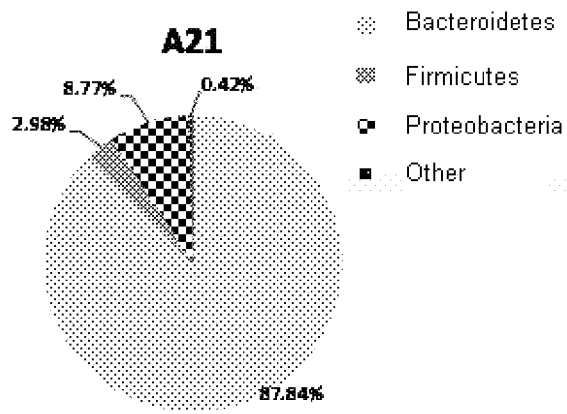
FIG. 7 is a diagram showing the composition of intestinal flora at a phylum level in mice of the experimental group A at day 21 in Application Embodiment 1 of the present invention.
Figure 8:
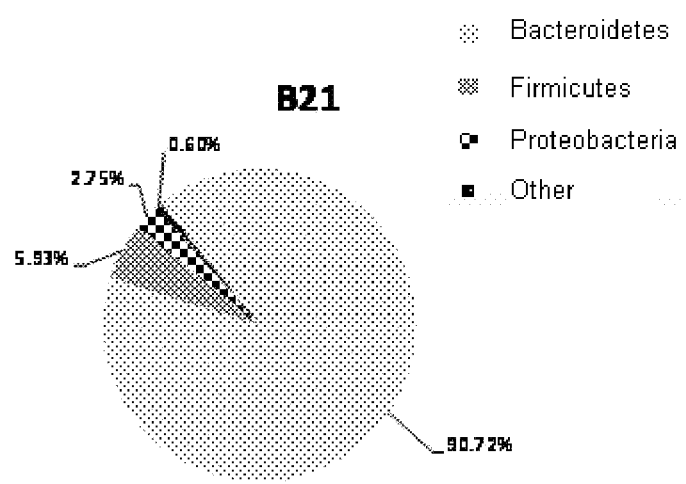
FIG. 8 is a diagram showing the composition of intestinal flora at a phylum level in mice of the experimental group B at day 21 in Application Embodiment 1 of the present invention.
Figure 9:
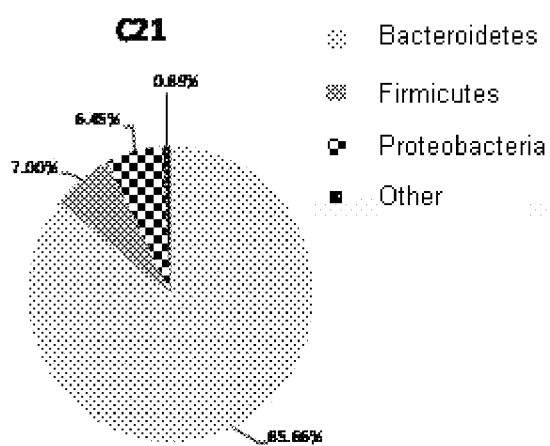
FIG. 9 is a diagram showing the composition of intestinal flora at a phylum level in mice of the experimental group C at day 21 in Application Embodiment 1 of the present invention.

Table 2 and FIG. 5 show changes in the indicators of mice of the experimental groups A, B, C and the blank group O when feeding for 14 days and 21 days. The small intestine is the main part of the nutrient digestion, absorption and transport in the body. Therefore, good intestinal mucosal structure is extremely important for improving the digestive and physiological functions and promoting the growth and development of the body. Small intestine villi, as an important part of the small intestine, not only plays an important role in the absorption of nutrients, but also destroy the colonization of harmful bacteria by the strong swing of the small intestine villi. The effect of probiotics on intestinal morphology and functions may be more than a change in the morphology of the intestinal villi, but also more changes at the cellular level. The ratio of the villus height to the fossae depth reflects the functional state of the small intestine. When the ratio decreases, it indicates that the mucosa is damaged, the digestion and absorption function is decreased and the growth and development of the animal is blocked. After 14 days of feeding, the ratios of the villus height to the fossae depth in the groups A and B were higher than that in the blank group, while the difference between the group C and the blank group was not obvious. After 21 days, the ratios of the villus height to the fossae depth in the group B and the group C were higher than that in the blank group, and the group C performed best. The reasons may be that it promotes the establishment of normal microflora in the gastrointestinal tract of mice, maintains the environmental stability in the digestive tract, and improves the living environment of the intestinal villi. This is further confirmed in the blood biochemical test of the DAO value in the group C.

3.4 Determination of Metabolomics of Intestinal Contents

TABLE 3

Changes of values in some organic acids in experimental groups

| | Chemical compound | Group A | Group B | Group C | Control group O |
|---|---|---|---|---|---|
| 14 D | l-Isoleucine, trimethylsilyl ester | 1351254 | 937933.3 | 1029646 | 6442426 |
| | L-Leucine, N-(trimethylsilyl)-, trimethylsilyl ester | | 233121.4 | 171788.6 | 1587480 |
| | l-Norvaline, n-propargyloxycarbonyl-, propargyl ester | 206724.3 | 144895.4 | 94160.24 | 143520.8 |
| | L-Tyrosine, N,O-bis(trimethylsilyl)-, trimethylsilyl ester | 445216.2 | 474403.5 | 387425.5 | 1274665 |
| | N,O-Bis-(trimethylsilyl)phenylalanine | 72018.65 | 88755.76 | 75478.61 | 542069.7 |
| | Butanedioic acid, bis(trimethylsilyl) ester | 1.77E+08 | 33792958 | 3.4E+08 | 25217896 |
| | Ethanedioic acid, bis(trimethylsilyl) ester | 1871312 | 3891977 | 3907010 | 4285687 |
| | Pentanoic acid, trimethylsilyl ester | 84519.87 | 346770 | 53365.86 | 2998365 |
| 21 D | l-Leucine, trimethylsilyl ester | 260505.9 | 316711.9 | 157854.1 | 566258.5 |
| | L-Norvaline, N-(trimethylsilyl)-, trimethylsilyl ester | 721582.8 | 446013.8 | 703647 | 2844951 |
| | l-Norvaline, n-propargyloxycarbonyl-, propargyl ester | 142513.7 | 83465.25 | 88971.79 | 68541.14 |
| | tyrosine 2 | | | 174611.8 | 222560.6 |
| | N,O-Bis(trimethylsilyl)-L-phenylalanine | 114663.6 | 71594.49 | 39275.48 | 221386.5 |
| | Ethanedioic acid, bis(trimethylsilyl) ester | 4691238 | 4016730 | 5924692 | 4756718 |
| | Butanedioic acid, bis(trimethylsilyl) ester | 10164084 | 31606358 | 242145.9 | 217237.5 |
| | Pentanoic acid, 2-[(trimethylsilyl)oxy]-, trimethylsilyl ester | 166892.4 | 89691.58 | 35602.76 | 55032.92 |

As can be seen from Table 3, when the mice were fed with different feeds, the changes of contents of isoleucine, leucine, valine, tyrosine succinic acid, oxalic acid, valeric acid and isovaleric acid in the intestinal contents of mice are presented. Diabetes cause metabolic disturbance of partial amino acid, having two major characteristics. 1. Total plasma amino acid content and glycogenic amino acid content decrease in diabetes and are significantly negatively correlated with blood glucose. 2. Regardless of the quality of blood glucose control, the content of branched chain amino acids and their proportion in total amino acids are increased.

However, the contents of some amino acids were elevated 5-10 years before the onset of diabetes, especially the levels of five amino acids of isoleucine, leucine, proline, tyrosine and phenylalanine in blood abnormally rose. The experiment clearly shows that the results are more obvious especially after 21 days. The five amino acids have changed significantly with the combination made according to a reasonable feed ratio, which mainly decreased remarkably. It has significant significance for prevention and reduction of the incidence of diabetes.

The evaluation of the indicators related to these amino acids is not only conductive to predicting the risk of diabetes, but also has practical significance for heart disease, tumor (kidney cancer, pancreatic cancer), achieving targeted early intervention and prevention and playing a precise primary prevention role.

Bacteria use oligosaccharides to produce short-chain fatty acids. The increase of the short-chain fatty acid content causes a pH decrease in the intestines. Acetic acid is mainly produced by Bacteroidetes, while butyrate is mainly produced by Firmicutes. Butyric acid is the main source of energy for colon cells, which increases intestinal health, potentially reduces intestinal permeability, and prevents metabolic endotoxemia. After 14 days of feeding, the mice of the group C showed an increasing content of succinic acid and oxalic acid and a decreasing content of valeric acid compared with the mice of the groups A and B; and after 21 days of feeding, it was found that the content of oxalic acid increased and the contents of succinic acid and isovaleric acid decreased.

3.5 Determination of 16S DNA of Intestinal Contents

In this experiment, four phylums of bacteria were detected in the intestinal contents of mice, wherein Bacteroidetes, Firmicutes and Proteobacteria were the three most abundant phylums. FIGS. 6-9 show a composition of intestinal flora in phylum of mice on day twenty-one, indicating that in the mice of the blank group O, the abundance of Bacteroidetes reached 65.6%, Firmicutes reached 31.66%, and Proteobacteria reached 1.44%.

In the mice of the experimental group A, the abundances of the three phylums reached 87.84%, 2.98%, and 8.77%, respectively.

In the mice of the experimental group B, the abundances of the three phylums reached 90.72%, 5.93%, 2.75%.

In the mice of the experimental group C, the abundances of the three phylums reached 85. 65%, 7.00%, and 6.45%, respectively.

Compared with the blank group, it showed that in the experimental groups A, B and C, the abundances of Bacteroidetes and Proteobacteria increased, and the abundance of Firmicutes decreased. The proliferation of the Bacteroidetes and Proteobacteria are promoted by the ingestion of oligosaccharides in mice, and the growth of the Firmicutes is inhibited.

Figure 10:
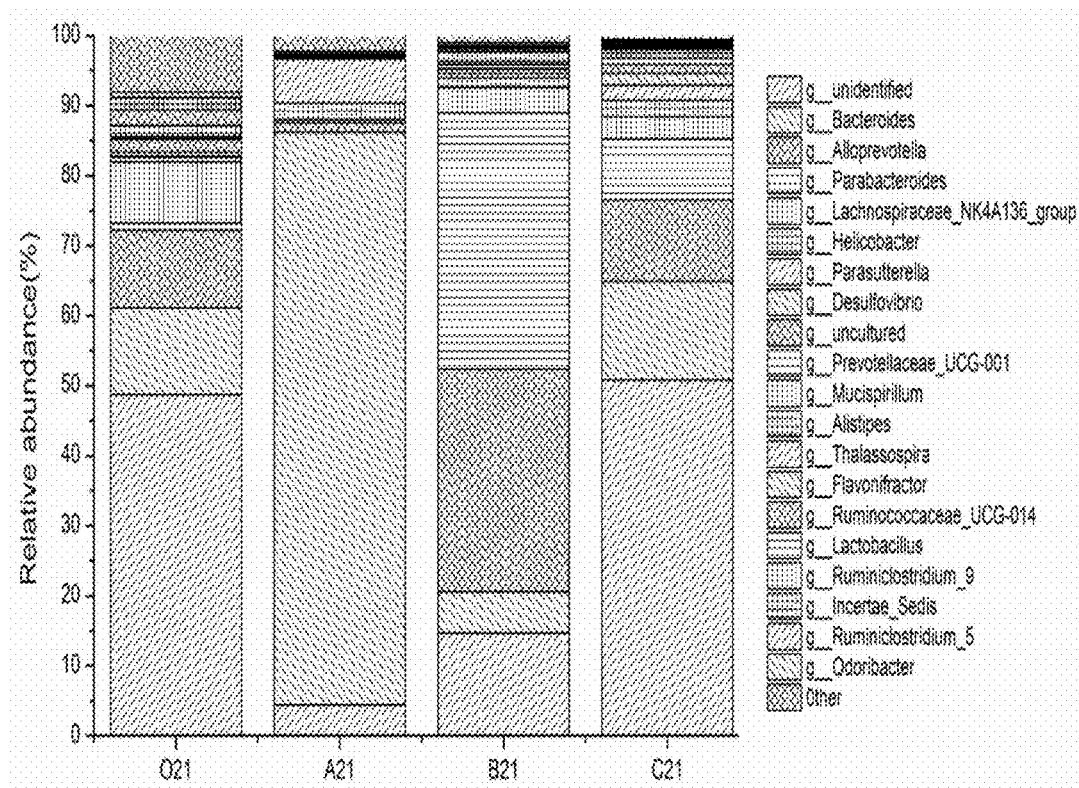
FIG. 10 is a diagram showing the composition of intestinal flora at a genus level in mice of four experimental groups at day 21 in Application Embodiment 1 of the present invention.

In this experiment, 14 genera of bacteria having a proportion of more than 0.1% were detected in the intestinal contents of the mice. *Bacteroides, Alloprevotella, Prebacteriodes, Lachnospiraceae,* and *Parasutterella* were the major genera of the intestinal contents. FIG. 10 showed a composition of intestinal flora in genus of the mice on the day twenty-one, indicating the following.

After the mice ingested the feed of the experimental group A, the *Bacteroides* in the intestinal contents increased significantly, while the *Bacteroides* in the intestinal contents of the mice in the group B were significantly decreased, and the changes in *Bacteroides* in the group C were not obvious, indicating that the combination of the functional oligosaccharides has the effect of promoting the proliferation of *Bacteroides*, while the common oligosaccharides have no such effect.

In the intestinal contents of the mice in the groups B and C, *Alloprevotella* and *Parabacteriodes* increased, while decreased in the group A, indicating that the common oligosaccharides have the function to promote the proliferation of *Alloprevotella* and *Parabacteriodes*.

Compared with the blank group, in the samples of the groups A, B, and C, *Lachnospiraceae* decreased, while *Parasutterella* increased. Galactooligosaccharides and inulin, as prebiotics, are not digested and absorbed by the body but directly enter the large intestine, playing an important role in regulating intestinal flora, maintaining normal environment in the intestine, regulating intestinal function, and improving the health of the body. Polydextrose, as a water-soluble dietary fiber, can shorten the emptying time of food in the stomach and effectively improve intestinal function. After being ingested into the human body, the polydextrose is fermented only in the lower half part of the gastrointestinal tract to produce short-chain fatty acids such as butyric acid, which lowers the pH in the intestine, and helps fight infection. The insoluble dietary fiber extracted from wheat bran cannot be dissolved in water and cannot be fermented by microorganisms in the large intestine, and can merely reduce the residence time of excreta in the intestine, increase the volume of intestinal contents, and play a role in improving the microbial reproductive environment and loosening bowel to relieve constipation.

This experiment focuses on verifying a synergistic effect of combinations of functional glycans and common glycans. The synergistic effect mainly includes the following two aspects. First, changes of suitable microbial abundance and the microbial living environment.

Second, effects of balanced microbial nutrition on changes of physiological indicators of the host. The experimental results show that all types of glycan combinations have significant effects on mouse intestinal micro-ecology and physiological indicators. Among them, the synergistic effect of the combination containing the functional glycans and the common glycans improves the steady state of the host intestinal microbe, and has a positive effect on the host without causing side effects. Single addition of the combination of functional glycans or the combination of common glycans in the experimental groups have a positive effect on the host and also cause certain side effects in stages.

3.6 Experimental Conclusion and Analysis:

In this experiment, the effects of different types of glycan combinations on the intestinal micro-ecological system of mice were investigated. Four feed formulations, including groups O, A, B and C, were used to feed the mice. The analysis of intestinal contents in the mice by macrogenome showed that different dietary diets have great effects on the intestinal flora. Further, the data of the pH of the colon contents and the SCFA in the blood indicated that the oligosaccharides and dietary fibers were fermented to produce a large amount of short-chain fatty acids, causing the pH to decrease. The data analysis of the DAO and TMAO contents in the serum and the intestinal villi showed that the mice in the group C performed best, indicating that the diversity of glycans and dietary fiber contributed to the health of the intestinal micro-ecological system in normal mice.

In summary, various types of glycan combinations have significant effects on mouse intestinal micro-ecology and physiological indicators in mice. Among them, the synergistic effect of the combination of functional glycans and the combination of common glycans improves the steady state of host intestinal microbe and has a positive effect on the host without causing side effects. The experiment group where the combination of functional glycans or the combination of common glycans are individually added have a positive effect on the host and also causes certain side effects in stages. The results show that the nutrition enhancers and supplements, such as common glycans, are important nutrient components and key factors in ensuring health.

Application Embodiment 2

In this embodiment, 40 volunteer subjects were selected for a human feeding trial. After 45 days of continuous test-meals, the changes of various indexes before and after the feeding trial were detected. The specific steps of the human feeding trial are as follows.

1. Selection of Populations
Inclusion Criteria:
1.1 Age: 18-75 years old.
1.2 Informed consent, volunteer subjects.
1.3 People who meet the above two criteria can be included as the test cases.
Exclusion Criteria:
1.4 Age: older than 75 years old or younger than 18 years old.
1.5 Patients with major cardiovascular and cerebrovascular diseases, such as stroke, severe hypertension, heart failure, major infectious diseases and mental disorders.
1.6 People who have participated in other clinical trials within the last 3 months.

2. Feeding Solutions
2.1 Test-food: the food containing the anti-inflammatory combination is provided by Beijing Ruiqianjing Science and Technology Development Co., Ltd., where all the raw materials used are food and food raw materials. The food containing the anti-inflammatory combination includes inulin, galactooligosaccharide, polydextrose and water-insoluble dietary fiber, wherein, the weight ratio of the inulin, the galactooligosaccharide, the polydextrose and the water insoluble dietary fiber is 25:25:20:30.
2.2 Feeding method: three bags of the test-food per day, 10 g per bag, and the test-food is administrated with warm water before meals (followed by eating meals).
2.3 Feeding period: continuous administration for 45 days.
2.4 Notes: the test group were administered the test-food according to the recommended method and dosage. During the trial, a normal diet was carried out without changing original eating habits. Medication habits were not changed, and if their constipation was improved during the period, the constipation drugs could be stopped as appropriate. Excessive drinking was avoided as much as possible during the feeding period.

3. Detection Time Point and Detection Content

TABLE 4

Table of detection time point and detection content of human feeding trial

|  | Baseline | 45 ± 3 days |
| --- | --- | --- |
| Basic information | ✓ |  |
| Fecal sampling | ✓ | ✓ |
| Blood routine | ✓ | ✓ |
| Liver function | ✓ | ✓ |
| Blood lipid (triglyceride)) | ✓ | ✓ |

TABLE 4-continued

Table of detection time point and detection content of human feeding trial

|  | Baseline | 45 ± 3 days |
| --- | --- | --- |
| Detection of intestinal function | ✓ | ✓ |
| Detection of amino acids contributing to cellular metabolism | ✓ | ✓ |
| Intestinal microbial constitution | ✓ | ✓ |
| Serum inflammatory factor | ✓ | ✓ |

4. Test Items
4.1 Basic information: blood pressure, weight, constipation.
4.2 Blood routine examination (blood routine and liver function, one tube).
4.3 Fecal sampling.
4.4 Liver function, fasting blood-glucose (the blood glucose of patients with diabetes was measured two hours after a meal, and the test result was recorded in the case report form (CRF) and the researcher's manual).
4.5 Blood lipid (triglyceride).
4.6 Improvement of cell metabolism: amino acids (leucine, isoleucine, phenylalanine, tyrosine, and valine).
4.7 Detection of intestinal function: DAO, D-lactic acid and TMAO.
4.8 Serum inflammatory factors.

5. Detection methods and instruments
5.1 Blood routine: BC-3000 hematology analyzer (test organization: Beijing Haisite Clinical Examination Office CO., LTD.)
5.2 Liver function: Roche cobas c501, chemiluminescence method (test organization: Beijing Haisite Clinical Examination Office CO., LTD.).
5.3 Blood glucose and blood lipid: blood glucose (Roche cobas c501), blood lipid (Roche cobas c701).
5.4 Detection of amino acid: high performance liquid chromatography-quadrupole ion-trap mass spectrometer HPLC-MS/MS API3200 Q-TRAP (test organization: Beijing Mass Spectrometry Medical Research CO., LTD.)
5.5 Serum DAO and serum D-lactic acid (test organization: Beijing Mass Spectrum Medical Research CO., LTD.).
5.6 Serum TMAO: mass spectrometry detection of LC-MS/MS (Agilent 6430) (test organization: Academy of Military Medical Sciences).
5.7 Serum inflammatory factor: protein liquid suspension chip (Luminex 200) (test organization: Academy of Military Medical Sciences).

6. Detection Results
6.1 Results of the Difference in Blood Biochemical Indicators The blood biochemical indicators of all the 40 people (all people), with high body mass index (BMI) and diabetes (10 people), and normal people (25 people, excluding people with lung cancer, psoriasis, etc.) were compared. The results are shown in FIGS. 11-13 and Table 5.

TABLE 5

Results of the difference in blood biochemical indicators after 45 days of human feeding trial

|  | Normal people | People with high BMI and diabetes | All people |
| --- | --- | --- | --- |
| Hemoglobin | ↓ | ↓ | ↓ |
| Mean hemoglobin content | ↓ | ↓ | ↓ |
| Mean hemoglobin concentration | ↓ | ↓ | ↓ |
| IgE | ↓ | ↓ | — |
| Globulin | ↓ | ↓ | ↓ |
| Indirect bilirubin | ↓ | — | ↓ |
| Serum lead | ↓ | — | ↓ |
| Total bilirubin | ↓ | — | ↓ |
| Erythrocyte distribution width | ↓ | — | ↓ |
| Thrombocytocrit | ↓ | — | — |
| Uric acid | ↓ | — | ↓ |
| ALT | — | — | ↓ |
| albumin | ↑ | ↑ | ↑ |
| Albumin/globulin ratio (A/G) | ↑ | ↑ | ↑ |
| IgA | ↑ | — | ↑ |
| Alkaline phosphatase | ↑ | — | ↑ |
| Insulin | ↑ | — | ↑ |

Note:
in the table, "↓" represents a decreasing trend of each indicator after and before the feeding trial. "↑" represents an increasing trend of each indicator after and before the feeding trial; and "—" represents no significant change of each indicator after and before the feeding trial.

The specific numerical analysis statistics in FIGS. 11-13 and the summary statistics in Table 5 above shows that: (1) in the results of this trial study, the blood insulin levels of the whole trial populations were increased, as shown in FIG. 11E, demonstrating that the pancreatic function is improved. Combined with the results of the comprehensive indicators of hematology and immunology and the results of diabetes-related amino acid metabolisms, the anti-inflammatory combination is confirmed to have significant significance for preventing diabetes.

Figure 12A:
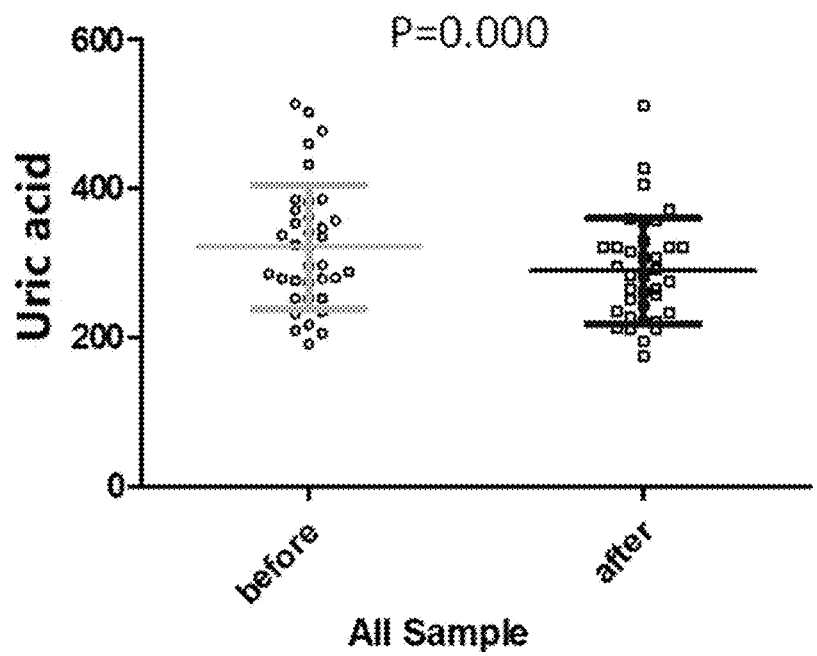

(2) In the results of this trial study, uric acid in the whole trial population was significantly decreased, as shown in FIG. 12A, demonstrating that the nucleic acid metabolism is improved. Combined with the comprehensive indicators of hematology and immunology, the results indicate that the anti-inflammatory combination has significantly improved the nucleic acid metabolism, preventing gout and improving renal function in view of the current situation of frequently-occurring uric acid increasing.

Figure 12B:
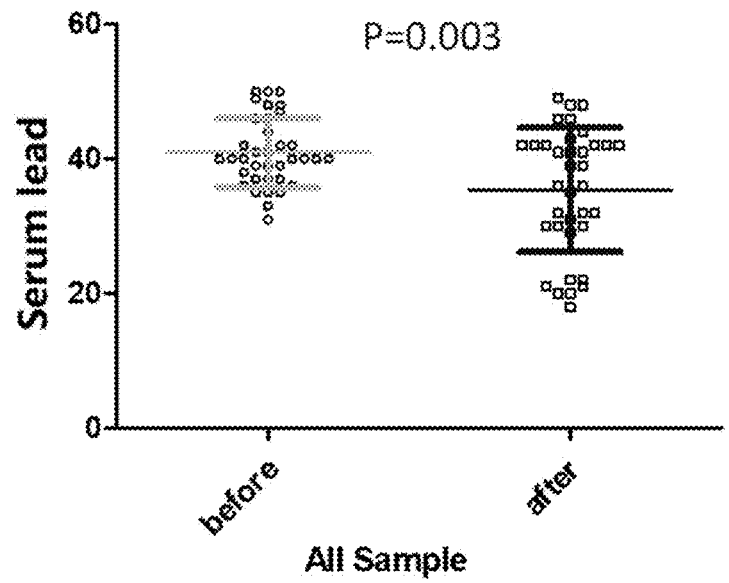

(3) In the results of this trial study, blood lead in the whole trial population was significantly decreased, as shown in FIG. 12B, indicating that the anti-inflammatory combination has significantly improved the blood environment and reduced the damage of heavy metals in the current environment where heavy metal pollution is serious.

Figure 12C:
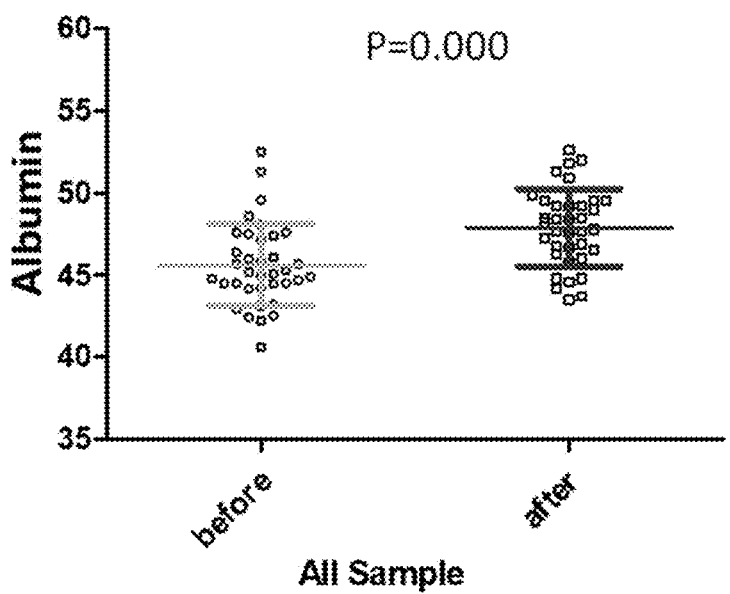
Figure 12D:
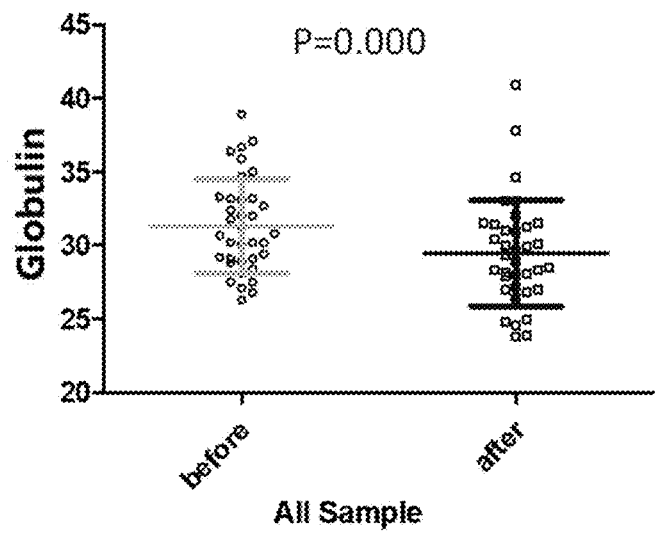
Figure 12E:
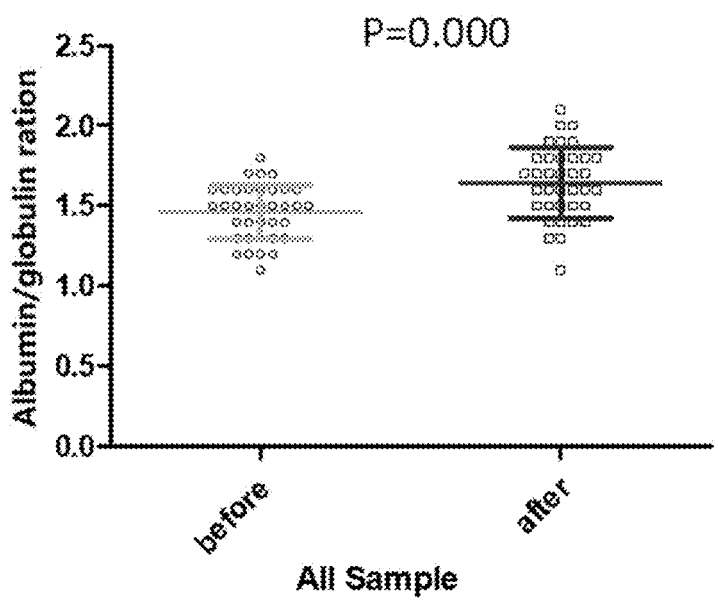
Figure 12F:
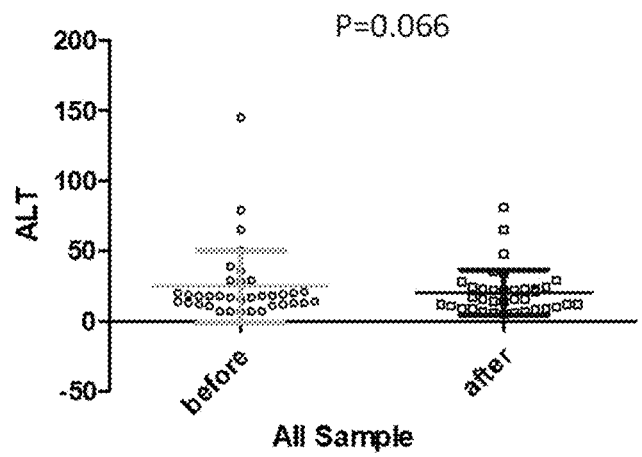
Figure 13A:
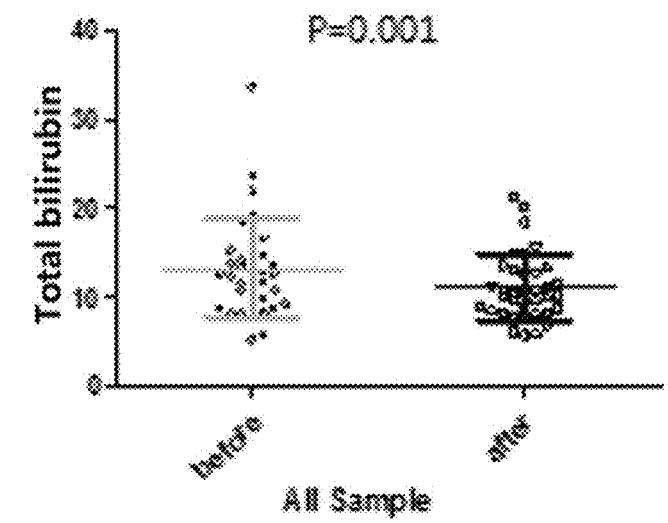
Figure 13B:
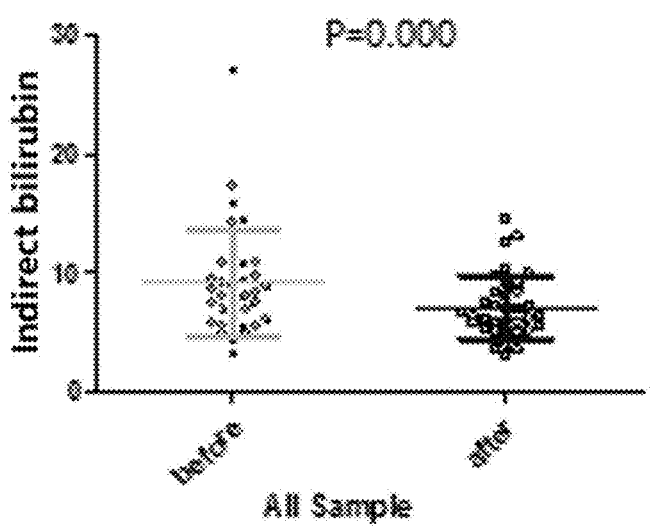
Figure 13C:
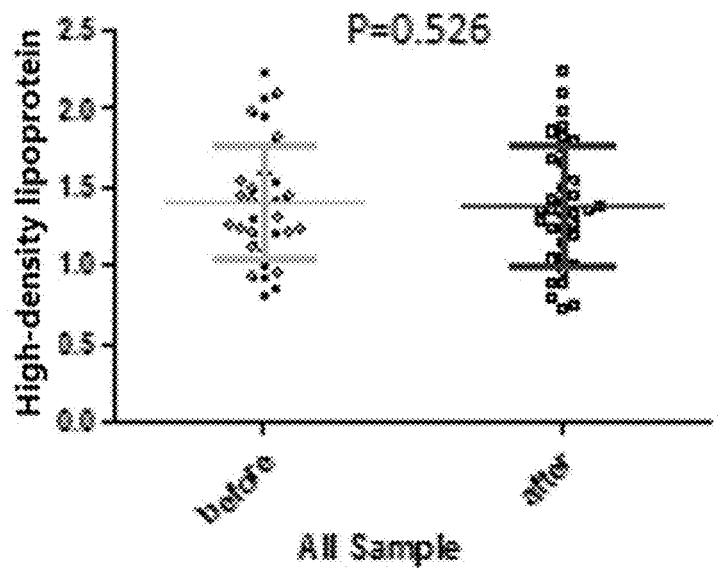

(4) In the results of this trial study, the ALT, indirect bilirubin and total bilirubin in the whole trial populations was decreased, as shown in FIGS. 12F, 13B and 13A, demonstrating that the liver function is improved. Combined with the comprehensive indicators of hematology and immunology, the results indicate that the anti-inflammatory combination has significantly improved liver function.

(5) In the results of this trial study, the hematological parameters of hemoglobin content, mean hemoglobin content, mean hemoglobin concentration and globulin in the whole trial population were improved. As shown in FIGS. 11A, 11B, 11C and 12D, and combined with the immunology and nutrient metabolisms, the results indicate that the anti-inflammatory combination has significant significance in improving sub-healthy physique.

Figure 11A:
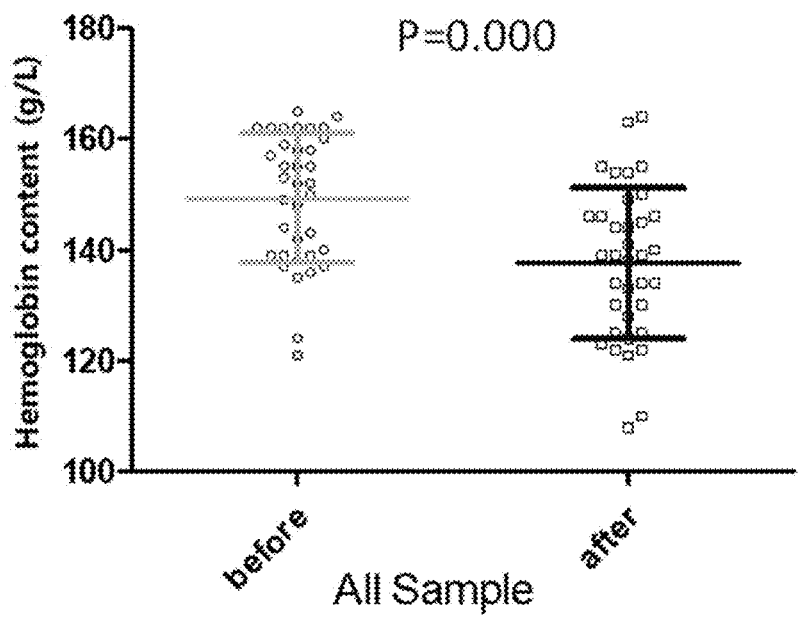
Figure 11B:
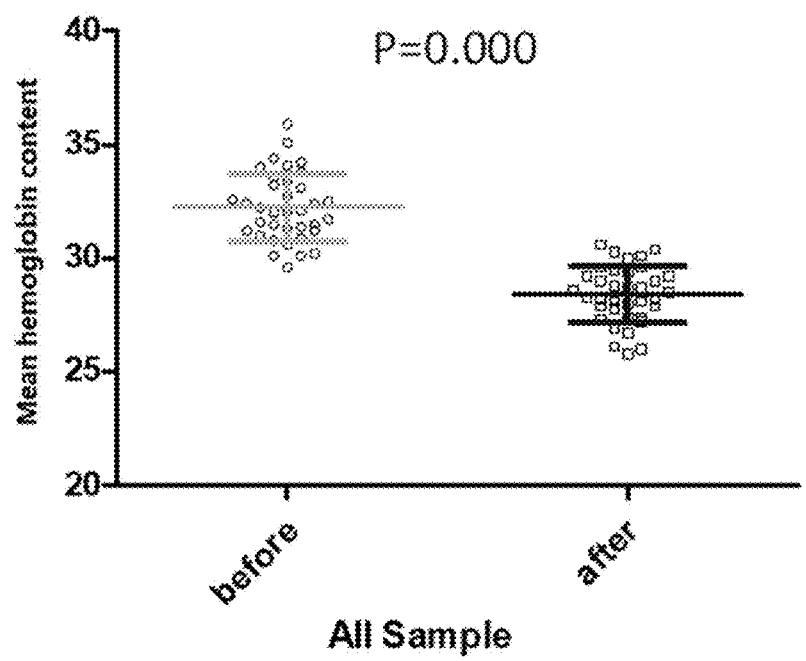
Figure 11C:
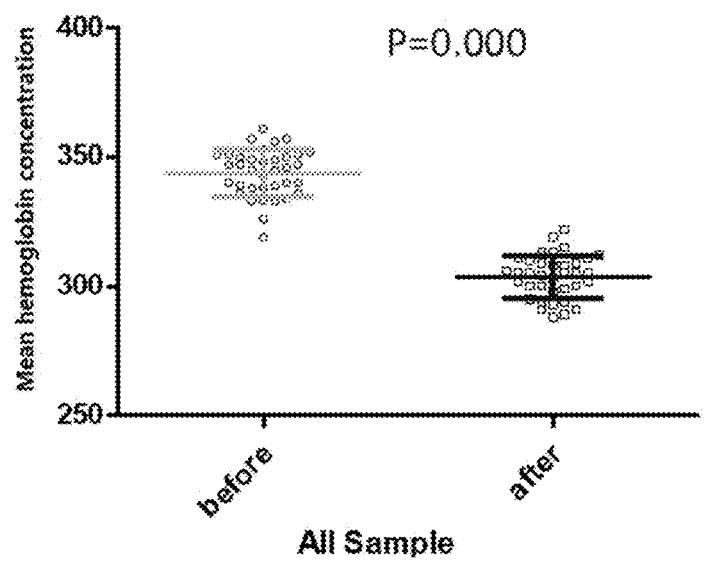
Figure 11D:
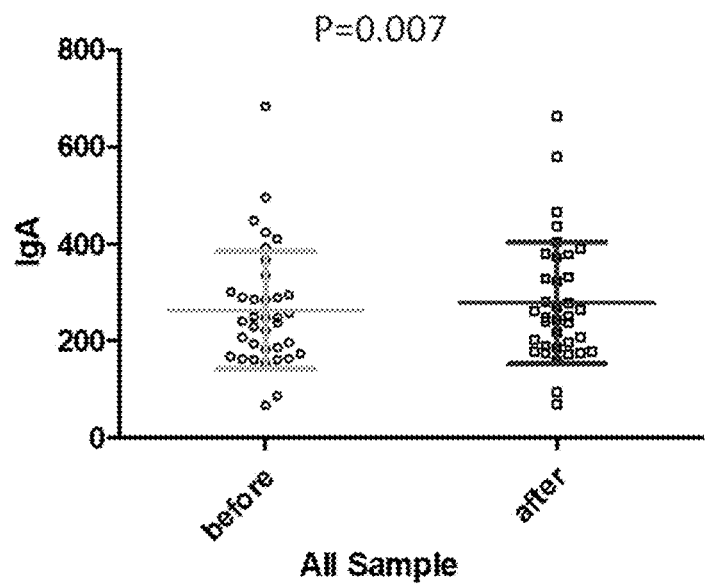
Figure 11E:
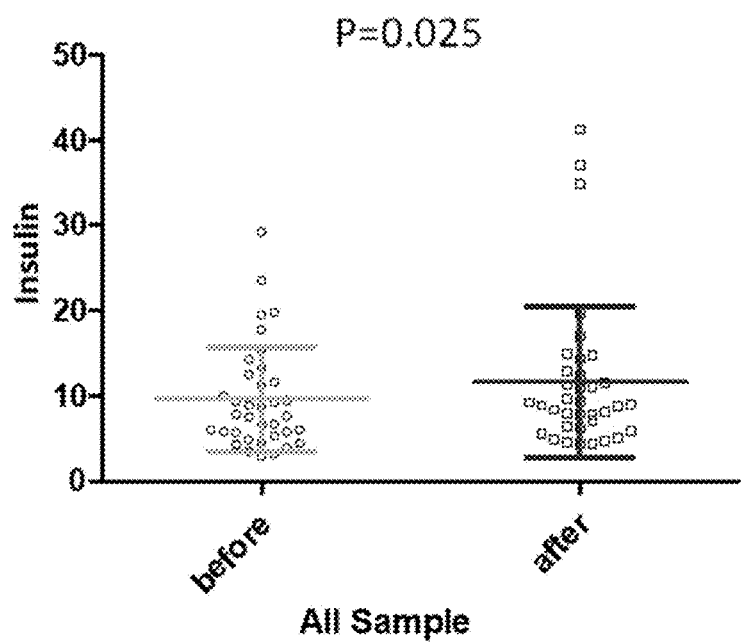
Figure 11F:
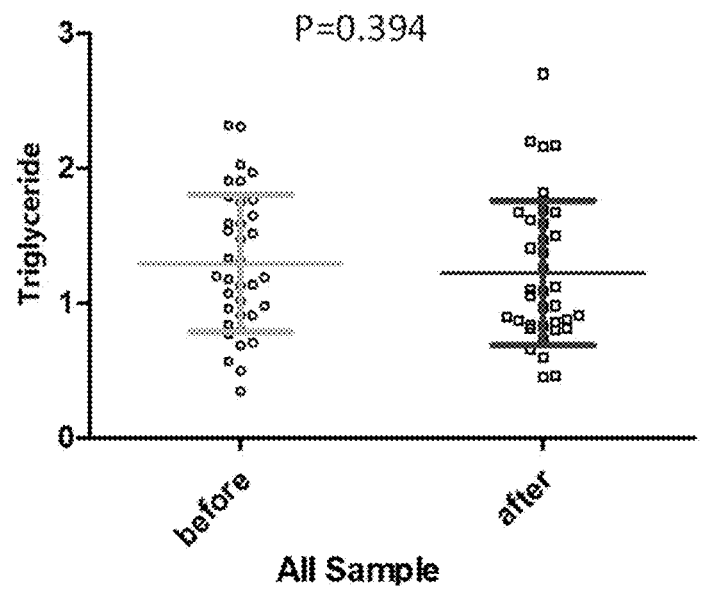
Figure 13D:
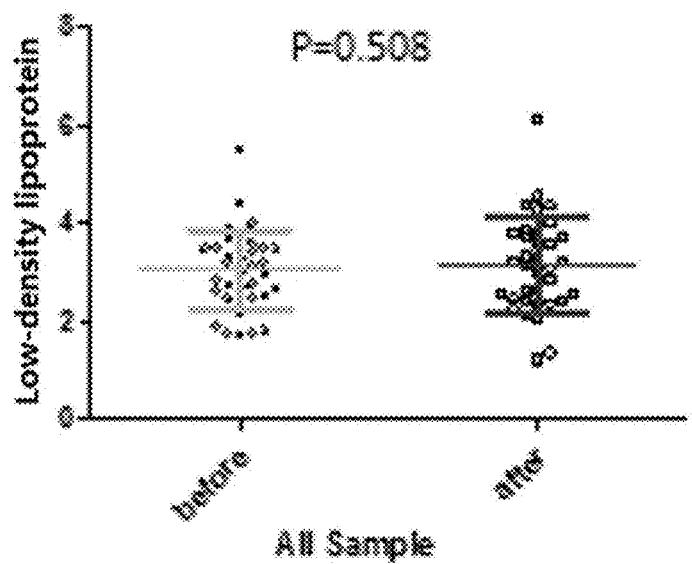
Figure 13E:
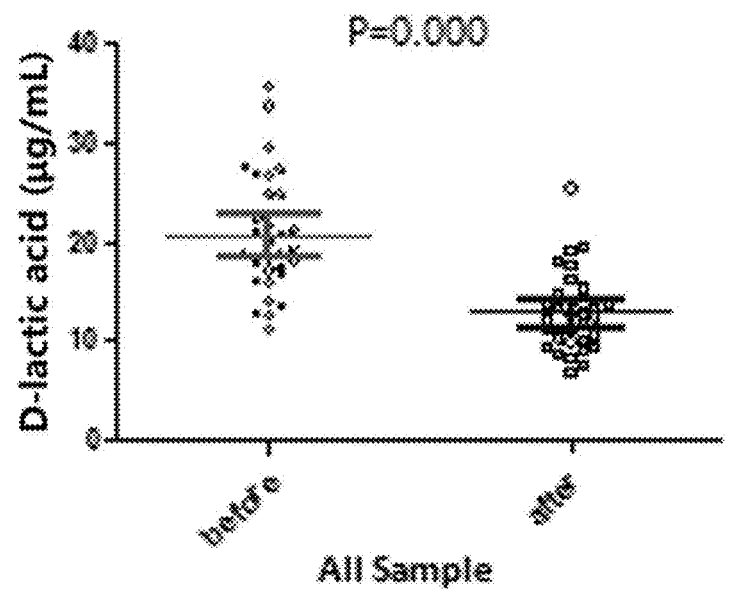
Figure 13F:
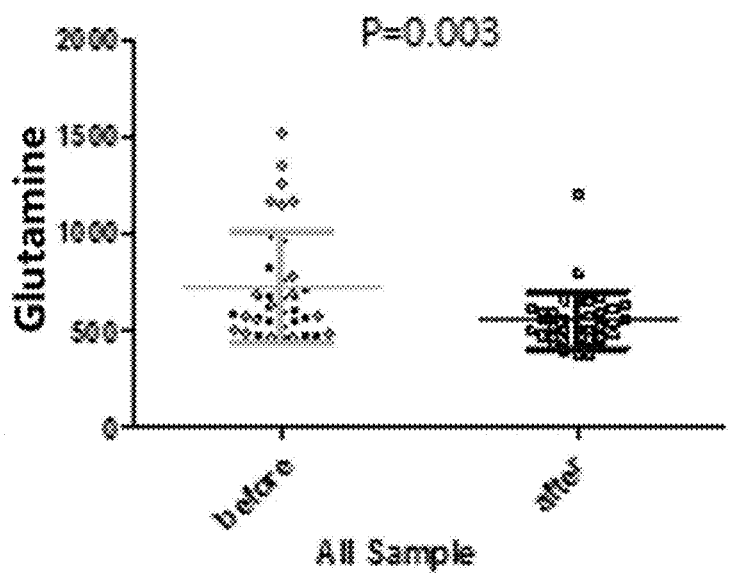
Figure 14A:
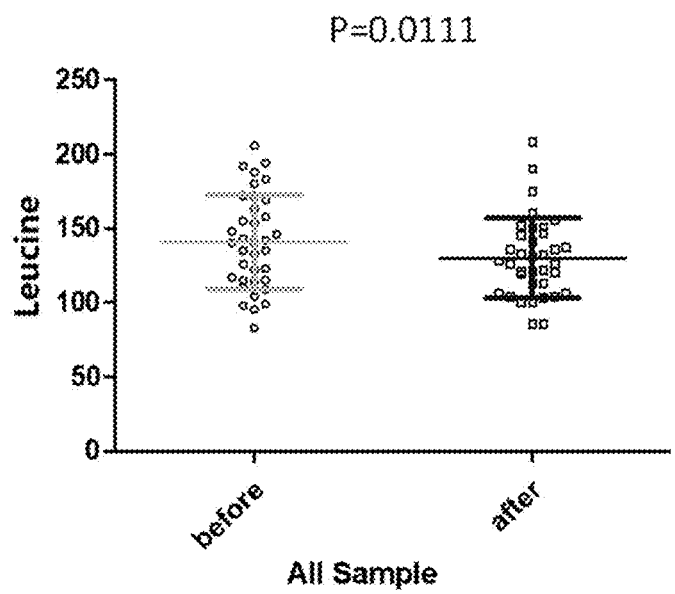
Figure 14B:
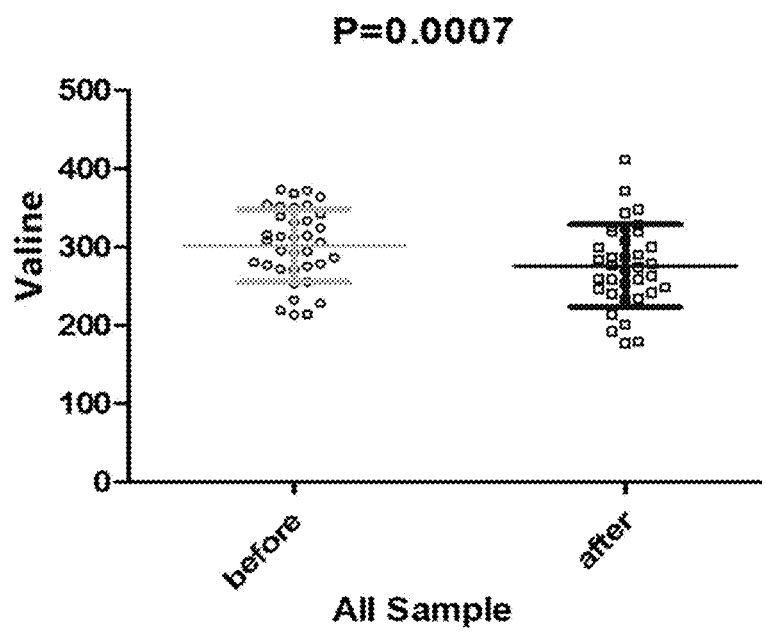
Figure 14C:
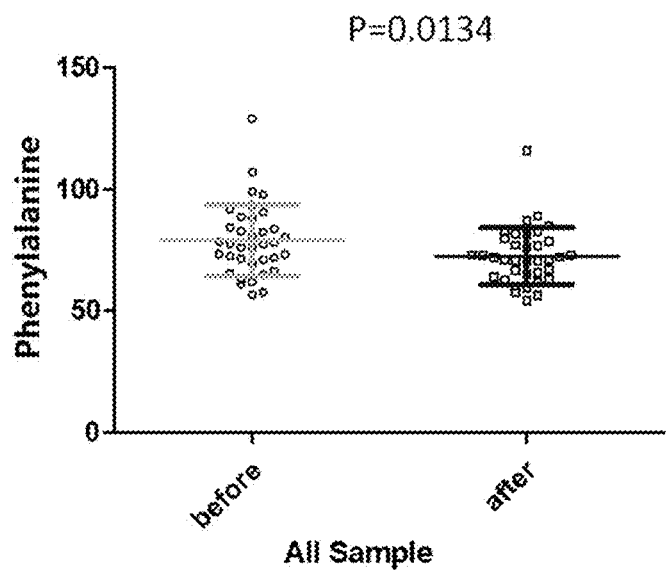
Figure 14D:
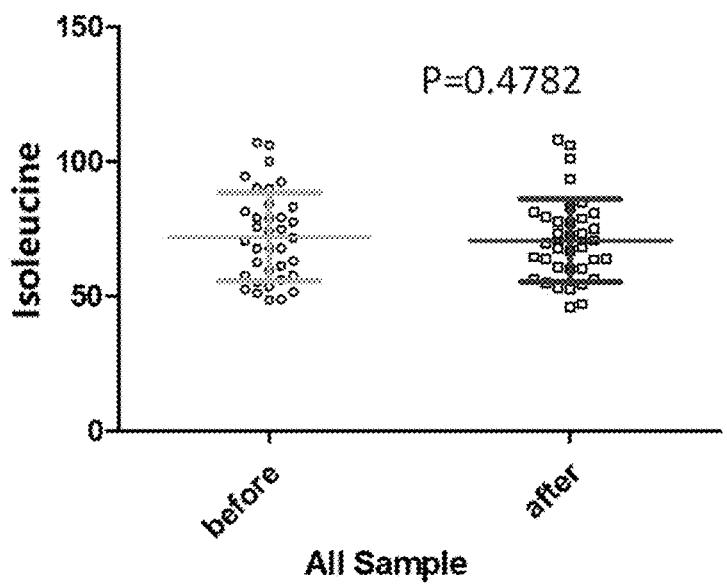
Figure 14E:
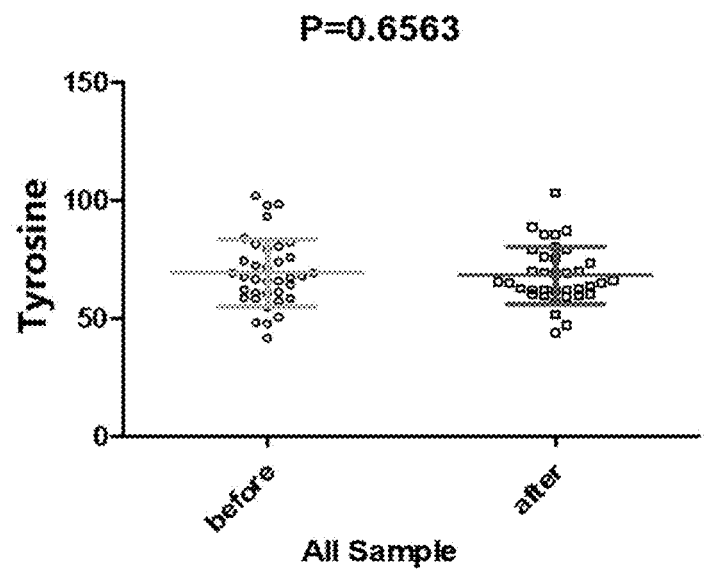
Figure 14F:
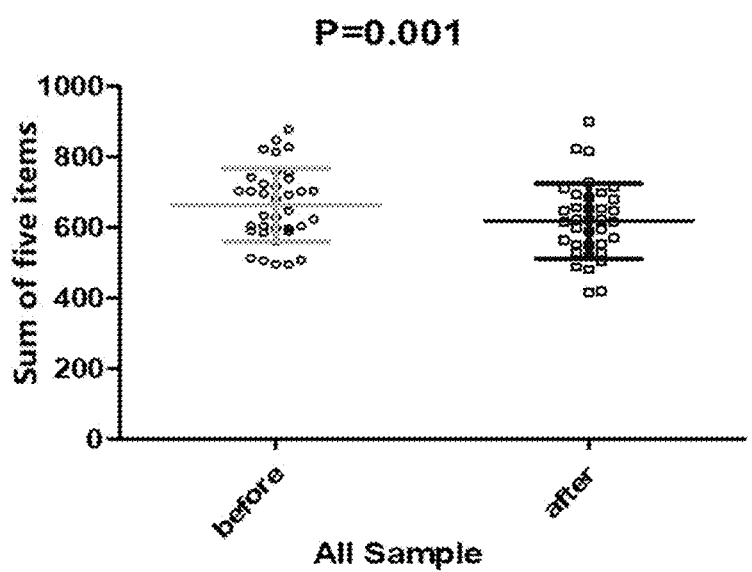

(6) In the results of this trial study, the low-density cholesterol and triglycerides in the whole trial population were decreased, as shown in FIGS. 13D and 11F, demonstrating that the blood insulin was increased, and as shown in FIG. 11E, demonstrating that the pancreatic function was improved. Combined with the comprehensive indicators of hematology and immunology, the results indicate that the anti-inflammatory combination has significantly improved lipid metabolism and preventing cardiovascular and cerebrovascular diseases.

(7) In the results of this trial study, the albumin, albumin/globulin ratio (A/G) and immunoglobulin IgA in the whole trial population were increased, as shown in FIGS. 12C, 12E and 11D, the immunity is improved, and combining with the results of immunology and nutrient metabolism, the basic elements of human health are improved.

6.2 Results of Difference in Amino Acid Indicators

Figure 15A:
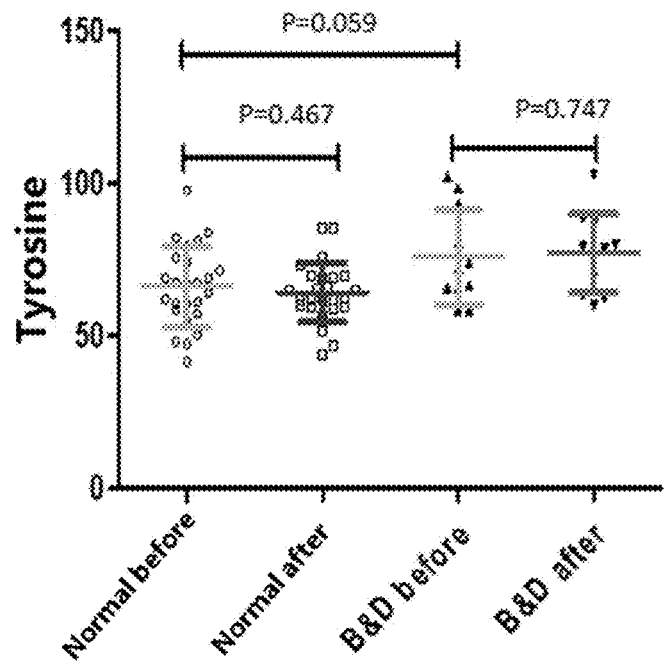
Figure 15B:
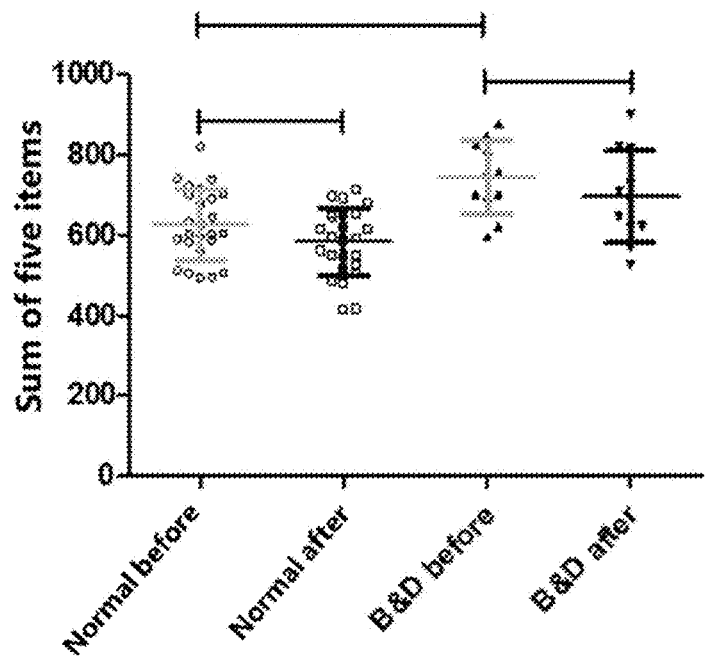

The amino acid indicators of all the 40 people (all people), people with high BMI and diabetes (10 people), and normal people (25 people, excluding people with lung cancer, psoriasis, etc.) were compared. The results are shown in FIGS. 14-15 and Table 6.

TABLE 6

Results of difference in amino acid indicators after 45 days of human feeding trial

|  | Normal people | People with high BMI and diabetes | All people |
| --- | --- | --- | --- |
| Histidine | ↓ | ↓ | ↓ |
| Aspartic acid | ↓ | ↓ | ↓ |
| Glutamine | ↓ | ↓ | ↓ |
| Valine | ↓ | — | ↓ |
| Asparagine | — | ↓ | ↑ |
| Glycine | — | ↓ | ↓ |
| Phenylalanine | — | ↓ | ↓ |
| Leucine | — | — | ↓ |
| Tryptophan | ↑ | — | ↑ |
| Threonine | ↑ | — | — |
| Proline | ↑ | — | ↑ |
| Alanine | ↑ | — | — |
| Lysine | ↑ | ↑ | ↑ |
| Cysteine | — | — | ↑ |

Note:
in the table, "↓" represents a decreasing trend of each indicator after and before the feeding trial. "↑" represents an increasing trend of each indicator before and after the feeding trial; and "—" represents no significant change of each indicator before and after the feeding trial.

Nutrient metabolism is the foundation of health. Amino acid (protein) metabolism is closely related to lipid metabolism and sugar metabolism. The abnormal metabolism of some amino acids related to diabetes has two major characteristics: 1) the plasma total amino acid content and the content of glycogenic amino acid are decreased in diabetes, and are significantly negatively correlated with blood glucose; and 2) regardless of the quality of blood glucose control, the contents of branched chain amino acids and their proportion in total amino acids are all increased.

However, in the 5-10 years before the onset of diabetes, the contents of some amino acids were increased. In particular, the levels of the five amino acids, including isoleucine, leucine, valine, tyrosine and phenylalanine, in the blood were elevated abnormally. According to the results of this experiment, after feeding the anti-inflammatory combination of the present application for 45 days, the sum of the relevant 5 amino acids decreased significantly, as shown in FIGS. 14 and 15, indicating significant improvement in preventing the incidence of diabetes.

6.3 Results of Difference in Intestinal Permeability Indicators

Figure 16A:
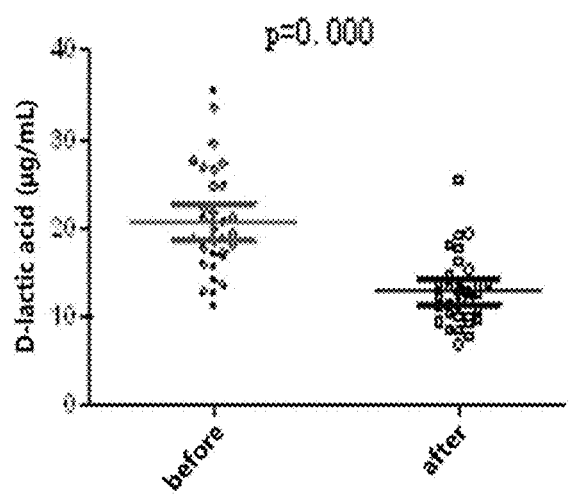
Figure 16B:
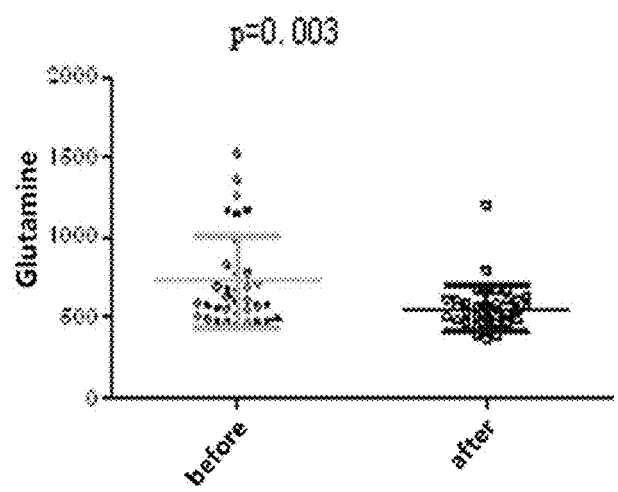
Figure 17A:
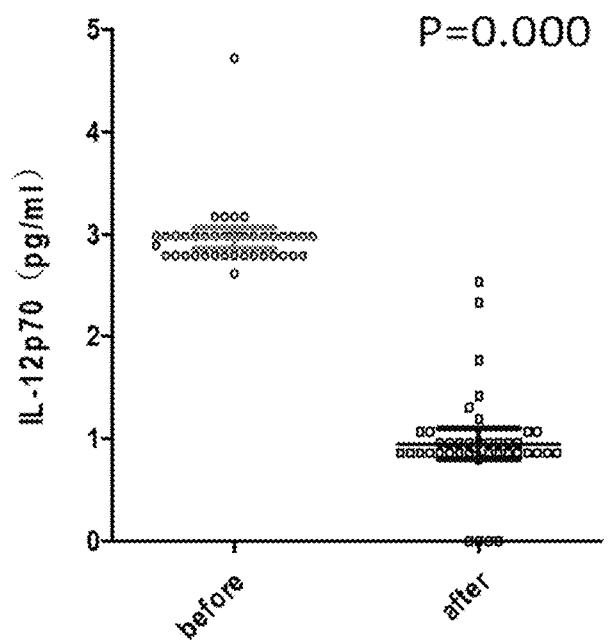
Figure 17B:
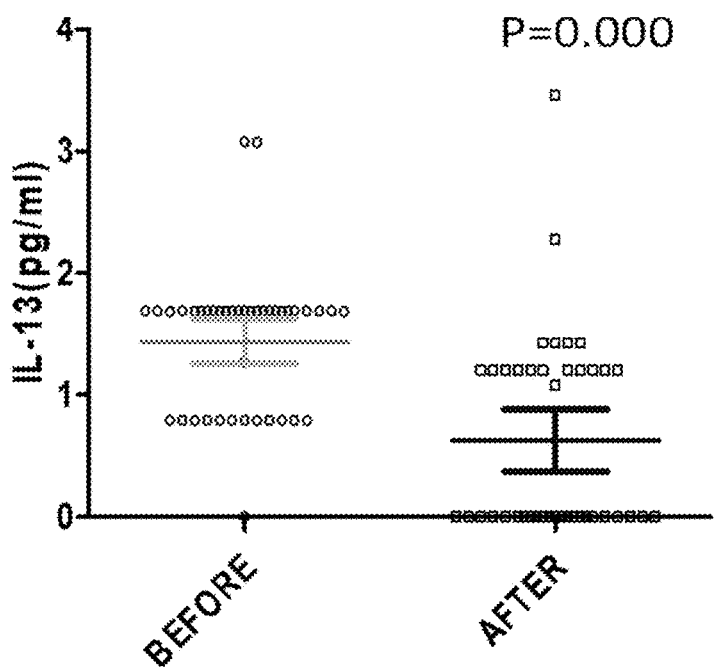
Figure 17C:
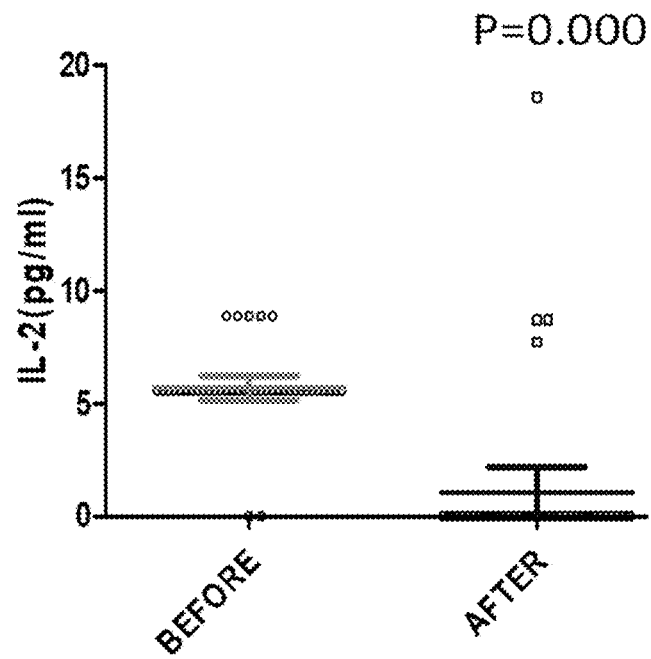
Figure 17D:
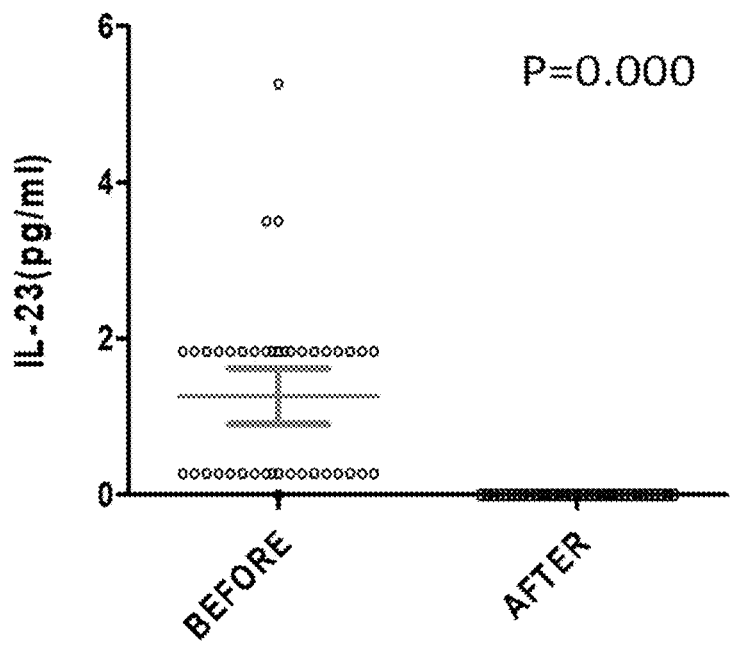
Figure 17E:
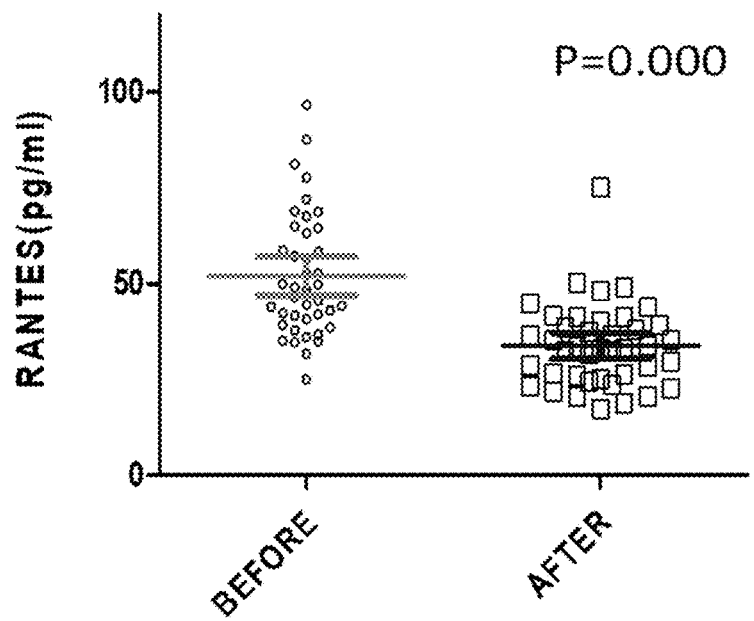
Figure 18A:
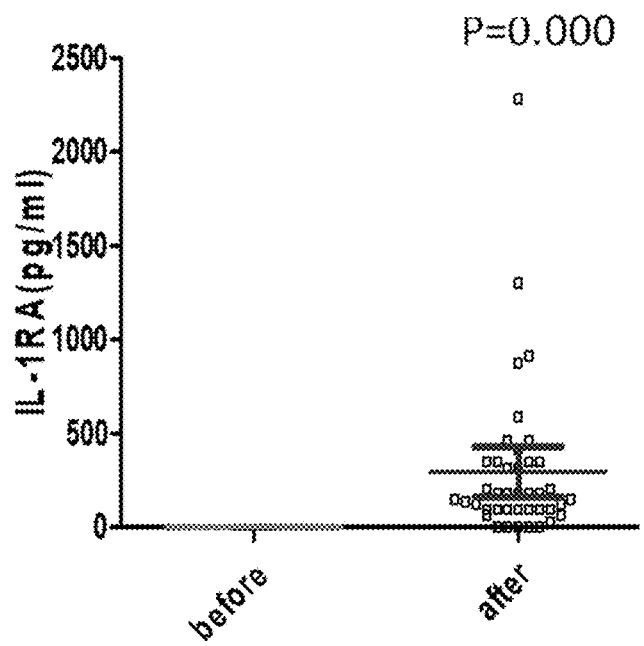
Figure 18B:
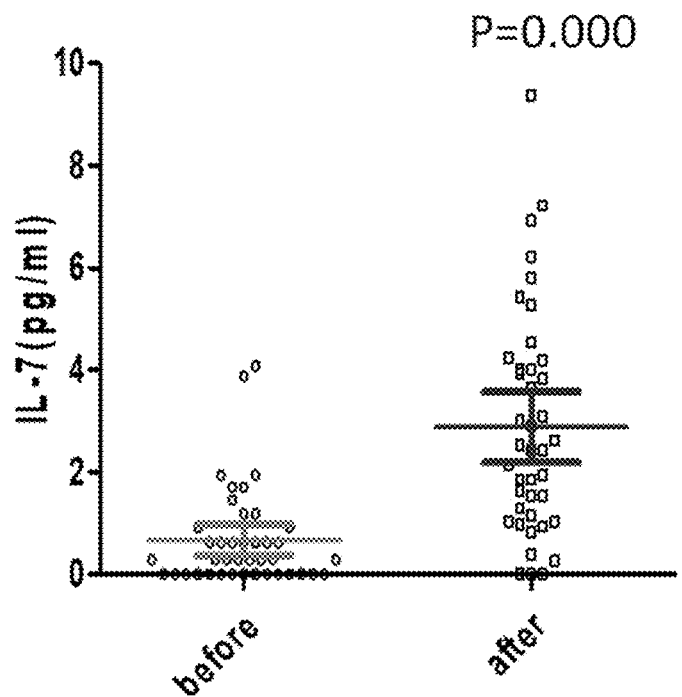
Figure 18C:
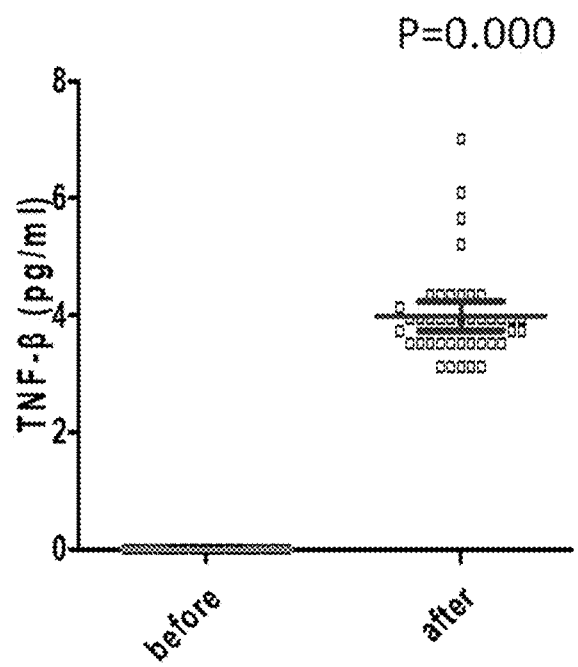
Figure 18D:
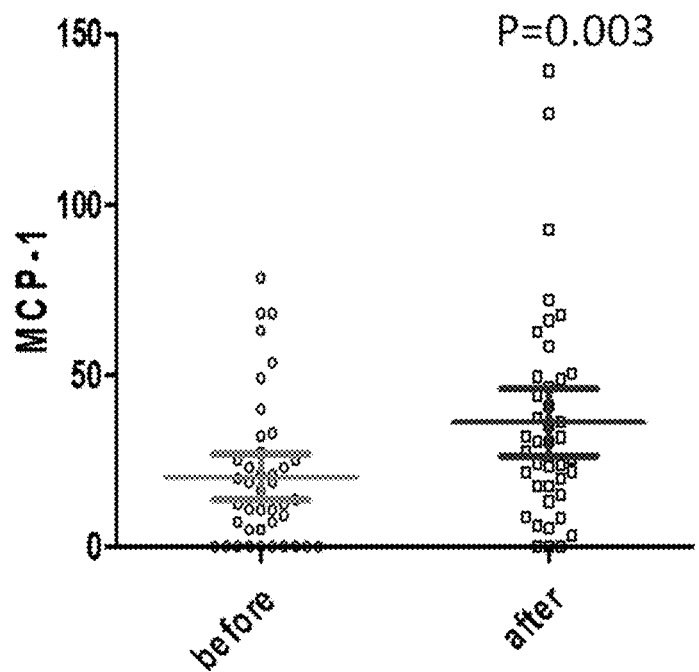
Figure 18E:
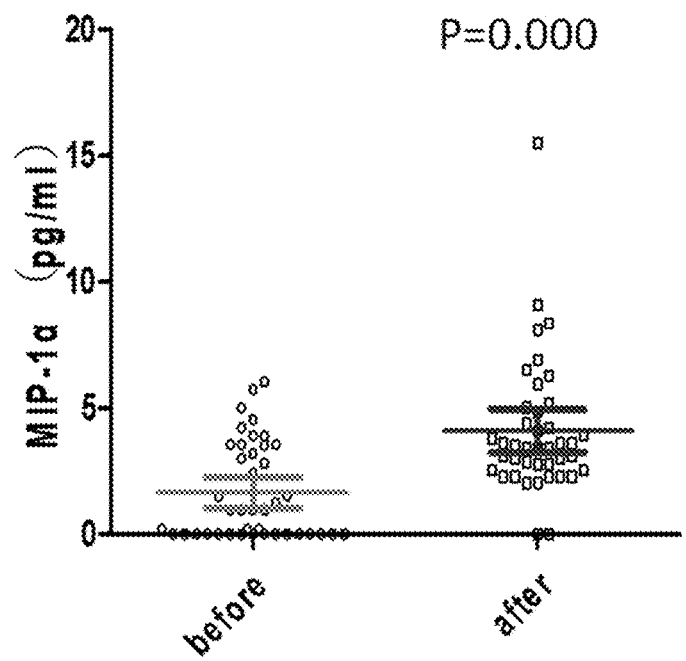
Figure 19A:
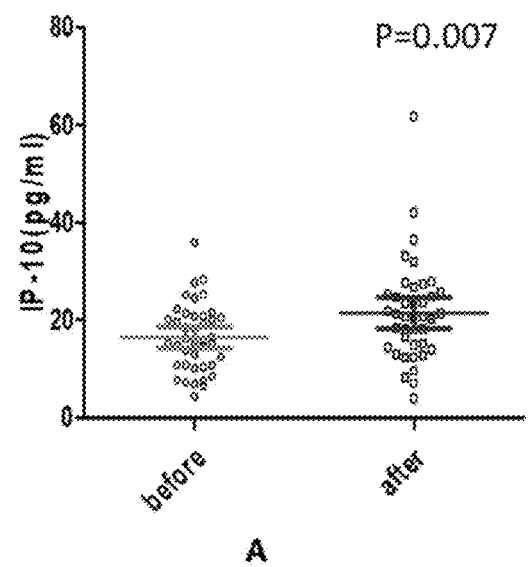
Figure 19B:
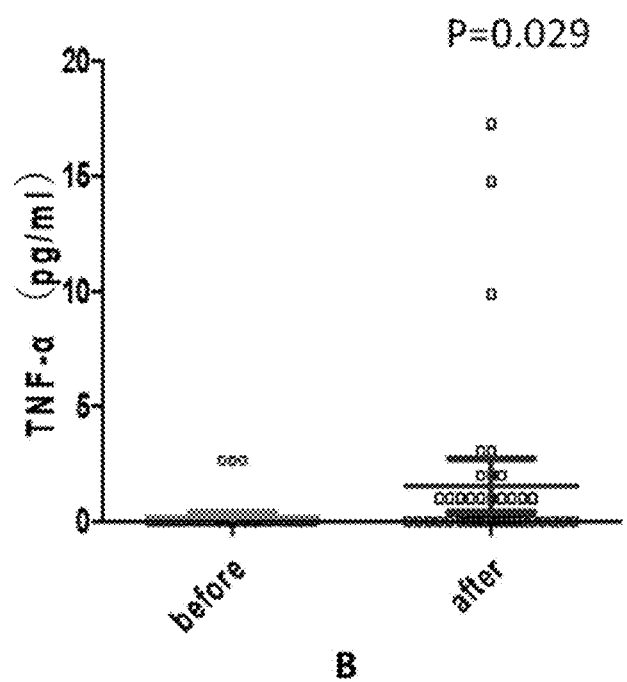
Figure 19C:
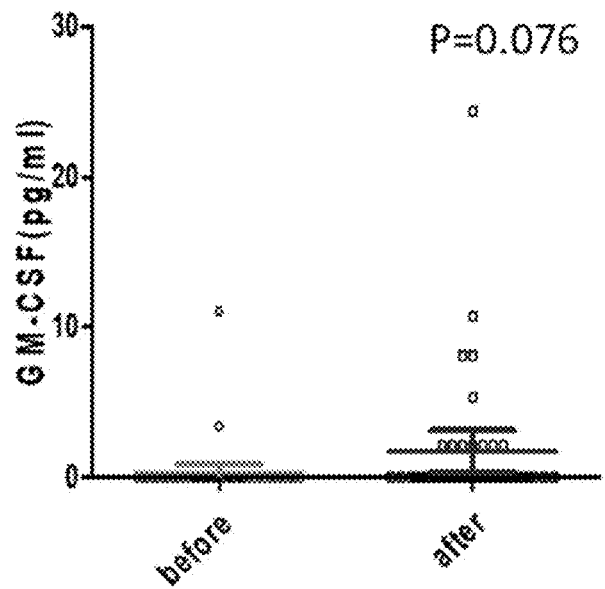
Figure 19D:
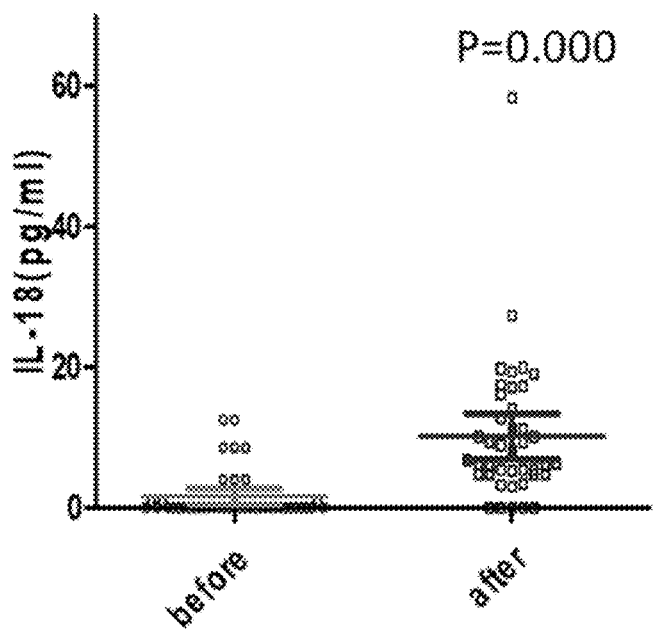
Figure 20A:
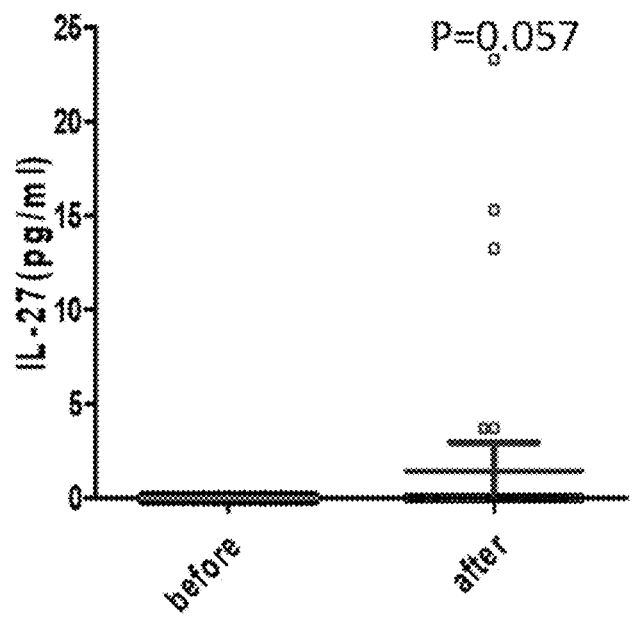
Figure 20B:
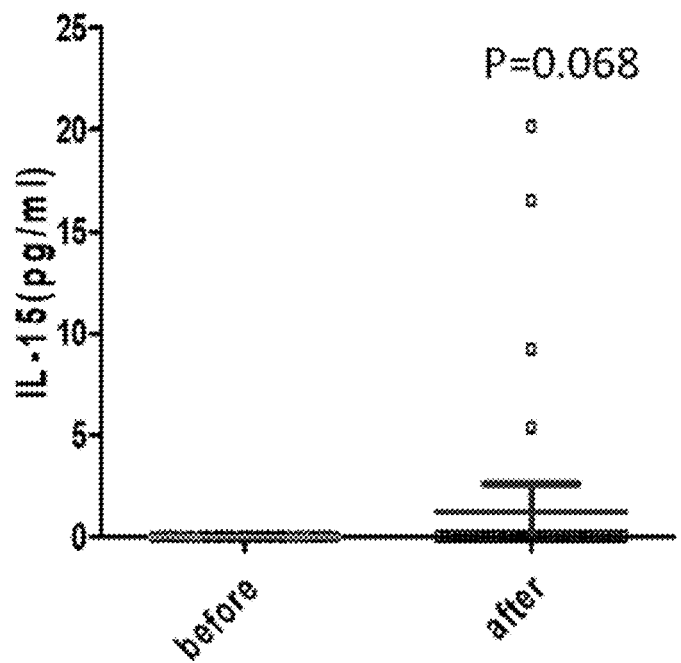
Figure 20C:
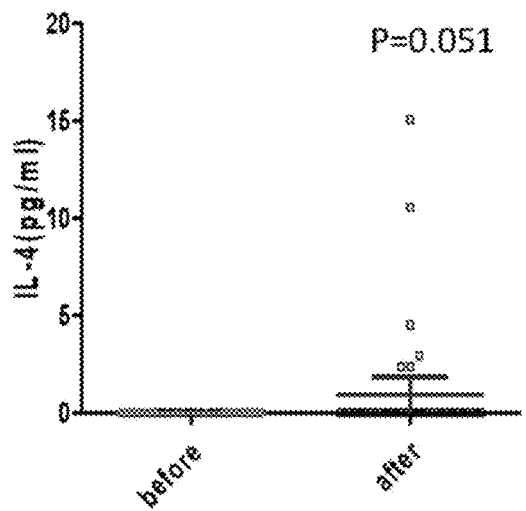
Figure 20D:
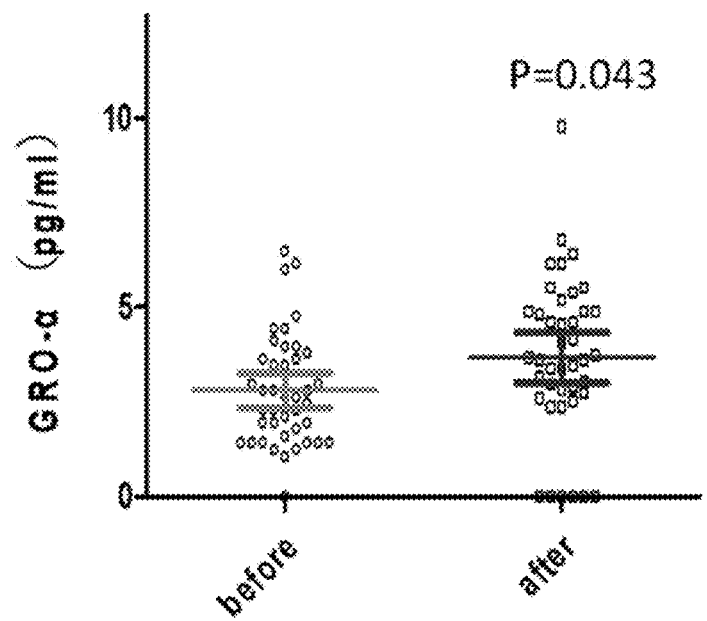

The intestinal permeability indexes of all the 40 people (all people), people with high BMI and diabetes (10 people), and normal people (25 people, excluding people with lung cancer, psoriasis, etc.) were compared. The results are shown in FIGS. 16A-16B and Table 7.

TABLE 7

Results of the difference in intestinal permeability indicators after 45 days of a human feeding trial

|  | Normal people | People with high BMI and diabetes | All people |
| --- | --- | --- | --- |
| TMAO | — | ↑ | — |
| D-lactic acid | ↓ | ↓ | ↓ |
| DAO | — | — | — |
| Glutamine | ↓ | ↓ | ↓ |

Note:
in the table, "↓" represents a decreasing trend of each indicator after and before the feeding trial; "↑" represents that an increasing trend of each indicator after and before the feeding trial; and "—" represents no significant change of each indicator after and before the feeding trial.

The group of indicators are landmark indicators for measuring intestinal permeability, where the trimethylamine oxide (TMAO) is an extremely sensitive indicator. In animal experimental studies, when most functional glycans were used alone, the TMAO indicator was prone to show a deterioration. This study showed no difference among the whole trial population, demonstrating that the synergistic effect of the formulation compensates for the defects of the functional glycan component. D-lactic acid, as a rigid indicator representing the level of the intestinal permeability, is significantly reduced, as shown in FIG. 16A, indicating that the intestinal metabolic substance D-lactic acid entering the blood is reduced and the intestinal function is significantly improved. As shown in FIG. 16B, the decrease of glutamine demonstrates that the cell utilization, especially the utilization of intestinal mucosal epithelial cells, is improved. The result is mutually verified with the improvement of intestinal functional elements such as constipation in the whole trial population. The decrease of intestinal permeability and the improvement of intestinal function are important foundations for improving the human physique.

6.4 Results of Difference in Cytokines

The cytokine indicators of all 40 people (all people), people with high BMI and diabetes (10 people), and normal people (25 people, excluding people with lung cancer, psoriasis, etc.) were compared. The results are shown in FIGS. 17-20 and Table 8.

TABLE 8

Results of the difference in cytokine indicators after 45 days of human feeding trial

|  | Normal people | People with high BMI and diabetes | All people |
| --- | --- | --- | --- |
| IL-12p70 | ↓ | ↓ | ↓ |
| IL-23 | ↓ | ↓ | ↓ |
| IL-13 | ↓ | ↓ | ↓ |
| SDF1α | ↓ | — | — |
| IFN-γ | ↓ | — | — |
| IL-2 | ↓ | — | ↓ |
| RANTES | ↓ | — | ↓ |
| IL-1RA | ↑ | ↑ | ↑ |
| IL-7 | ↑ | ↑ | ↑ |
| TNF-β | ↑ | ↑ | ↑ |
| IL-18 | ↑ | ↑ | ↑ |
| MIP1α | ↑ | ↑ | ↑ |
| MCP1 | ↑ | — | ↑ |
| IP-10 | — | — | ↑ |
| TNF-a | — | — | ↑ |
| IL-4 | — | — | ↑ |
| GRO-a | — | — | ↑ |

Note:
in the table, "↓" represents a decreasing trend of each indicator after and before the human feeding trial; "↑" represents a increasing trend of each indicator after and before the human feeding trial; and "—" represents no significant change of each indicator before and after the human feeding trial.

The body's immune balance plays a key role in maintaining human health. Currently, under external stresses and unscientific lifestyles, people are often in a "sub-health state", and their immune systems may have dysfunctions due to being constantly subjected to various stresses, resulting in an inflammatory response. This inflammatory response lies between basal homeostatic state and classic inflammatory response and is known as low-grade chronic inflammation or para-inflammation (Medzhitov 2008). Cytokines are small-molecule proteins with broad biological activity that are synthesized and secreted by immune cells or some non-immune cells due to external stimulations. The cytokines mainly IL, TNF, IFN, chemokines, CSF, etc. These cytokines can be used as biomarkers for the diagnosis of inflammations or diseases. The five inflammatory factors IL-12p70, IL-13, IL-2, IL-23 and RANTES decreased in this experiment, as shown in FIGS. 17A-17E, where IL-12 and IL-23 are mainly produced by antigen-presenting cells such as dendritic cells (DCs) and macrophages. IL-12 can promote the differentiation of inflammatory Th1 cells, and IL-23 can maintain the activity of inflammatory Th17 cells and inhibit the activity of anti-inflammatory Treg cells. IL-2 is mainly produced by inflammatory Th1 cells. IL-13 is mainly produced by anti-inflammatory Th2 cells. RANTES was significantly up-regulated after T-cell activation, which can chemotactic activated T cells. The anti-inflammatory combination could significantly inhibit the four pro-inflammatory factors, including IL-12, IL-2, IL-23, and RANTES, indicating that the anti-inflammatory combination may improve sub-inflammation by inhibiting related inflammatory T cells.

As shown in FIGS. 18A-18E, 19A-19D, and 20A-20D, among the cytokines elevated in the present trial, the IL-1RA is a natural antagonist of IL-1 receptor, which can inhibit the inflammatory response of the pro-inflammatory factor IL-1 pathway. Studies have shown that IL-1RA is significantly decreased in the intestinal mucosa of patients with Crohn's desease (CD) or ulcerative colitis (UC), suggesting the activation of the pro-inflammatory IL-1 pathway in the disease state (Casini-Raggi et al. 1995). The results of the present study show that the intervention of the combination can significantly increase the secretion level of the IL-1RA in vivo (the value was 0 before the intervention, and the mean value was 314 pg/mL after the intervention). The IL-4 can promote the differentiation and maturation of anti-inflammatory Th2 cells, and the IL-27 can induce T cells to produce the IL-10 under certain conditions to play an immunosuppressive role. The intervention of the combination can significantly increase the secretion levels of the IL-4 and the IL-27 in vivo. Obviously, not all cytokines are ideal, which is related to the time of administration, cell metabolic cycle and body regulation. As the time of administration increases, the improvement and regulation of cytokines require further measurements.

6.5 Results of the Difference of Intestinal Microorganisms

Before and after the human feeding trial of the whole population, the difference of the relative abundance of intestinal flora in phylum, class, order, family, genus and species between the paired samples was determined by using the Wilcoxon test method, and the comparison results of P value was adjusted by false discovery rate (FDR) (p.adj<0.05). The difference in species level are shown in the Table 9 below.

TABLE 9

The comparison results of intestinal flora between groups

|  | before | after | W | pval | padj |
|---|---|---|---|---|---|
| *Parabacteroides* NA | 0.001 | 0.007 | 0 | 0 | 0 |
| *Lactococcus* NA | 0.00003 | 0.010 | 9 | 0 | 0 |
| Ruminiclostridium__5 NA | 0.001 | 0.004 | 9 | 0 | 0 |
| *Intestinibacter bartlettii* | 0.003 | 0.0005 | 806 | 0 | 0 |
| Ruminiclostridium__6 NA | 0.001 | 0.0001 | 806 | 0 | 0 |
| *Turicibacter sanguinis* | 0.0002 | 0.002 | 20 | 0 | 0.00000 |
| *Blautia obeum* | 0.003 | 0.002 | 793 | 0 | 0.00000 |
| *Parabacteroides distasonis* | 0.011 | 0.045 | 38 | 0 | 0.00000 |
| *Allisonella histaminiformans* | 0.0004 | 0.001 | 44 | 0.00000 | 0.00000 |
| Laclmospiraceae__FCS020__group NA | 0.0004 | 0.0002 | 774 | 0.00000 | 0.00000 |
| Tyzzerella__3 NA | 0.002 | 0.006 | 47 | 0.00000 | 0.00000 |
| Ruminococcaceae__UCG-004 NA | 0.0003 | 0.00002 | 780 | 0.00000 | 0.00000 |
| Lachnospiraceae__ND3007__group NA | 0.005 | 0.002 | 768 | 0.00000 | 0.00000 |
| Ruminococcus__1 NA | 0.010 | 0.004 | 759 | 0.00000 | 0.00000 |
| Ruminococcus__2 NA | 0.015 | 0.004 | 756 | 0.00000 | 0.00000 |
| *Veillonella* NA | 0.0003 | 0.001 | 73 | 0.00000 | 0.00001 |
| Lachnospiraceae__FCS020__group bacterium | 0.0001 | 0.00000 | 527 | 0.00000 | 0.00001 |
| *Acinetobacter* NA | 0.00000 | 0.0004 | 0 | 0.00000 | 0.00002 |
| *Thermus* NA | 0.00000 | 0.0003 | 4 | 0.00000 | 0.00002 |
| *Parabacteroides merdae* | 0.003 | 0.008 | 85 | 0.00000 | 0.00003 |

As can be seen from Table 9 above, the differences in intestinal flora among the whole trial population were significant, which was consistent with the results of biochemical and intestinal function tests.

In the anti-inflammatory combination of the present invention, through the reasonable combination containing the water-insoluble dietary fiber and the functional oligosaccharides, the release rate of nutrition in the intestine is adjusted, the digestion speed is slowed down, the cholesterol excretion is accelerated, the toxic substances in the food are absorbed and then excreted out of the body, especially the metabolism of branched chain amino acids and aromatic amino acids related to the prevention of diabetes is improved, the stability or decrease of biochemical indicators of blood TMAO is ensured, and the intestinal permeability is reduced. Meanwhile, the anti-inflammatory combination of the present invention has the functions of water absorption and swelling, gradient bonding, mechanical isolation, mesh adsorption, ion exchange and microflora regulation, thus providing a favorable environment and foods for the growth of intestinal microorganisms and maintaining the homeostasis balance of intestinal microorganisms. Through the synergistic effect of the anti-inflammatory combination, the negative effect of using the functional oligosaccharides alone is eliminated, the blood endotoxin, blood lead and inflammatory factors are reduced, the cell metabolism and body's immunity are enhanced, pathogenic factors causing chronic inflammations, low immunity and the like are eliminated, thereby effectively preventing the occurrence of chronic diseases such as cardiovascular and cerebrovascular diseases, diabetes, etc. The combination of the present invention can effectively improve nutrient metabolisms, reduce intestinal permeability and maintain a homeostatic environment for intestinal microorganisms, and prevent chronic diseases. The anti-inflammatory food containing the above-mentioned anti-inflammatory combination of the present invention, as an essential staple food for people every day, provides balanced nutrients for the human body conveniently, thereby strengthening the physique, effectively preventing food-borne chronic diseases and ensuring health.

The above description shows only preferred embodiments of the present invention and is not intended to limit the present invention in any way. Some simple improvements, equivalent changes or modifications using the technical content disclosed above by those skilled in the art should all fall within the scope of the present invention.

What is claimed is:

1. A food, consisting of an anti-inflammatory combination, wherein,
the anti-inflammatory combination consists of: a functional oligosaccharide and a common oligosaccharide, the functional oligosaccharide is a combination of an inulin and a galacto-oligosaccharide, and the common oligosaccharide is a combination of a polydextrose and a water-insoluble dietary fiber for providing a microbial reproductive environment, and
a weight ratio of the inulin, the galacto-oligosaccharide, the polydextrose and the water-insoluble dietary fiber is (10-30):(5-30):(10-40):(10-50).

2. The food of claim 1, wherein, the food is effective at inhibiting inflammatory responses, and the anti-inflammatory combination reduces an inflammatory cytokine selected from the group consisting of interleukin-12p70 (IL-12p70), interleukin-13 (IL-13), interleukin-2 (IL-2), interleukin-23 (IL-23) and cytokine RANTES (regulated upon activation, normal T cell expressed and secreted), and increases an anti-inflammatory cytokine selected from the group consisting of interleukin-1 receptor antagonist (IL-1RA) and interleukin-4 (IL-4).

3. The food of claim 1, wherein, the food is effective at improving a utilization rate of glutamine, reducing intestinal permeability targeting marker including D-lactic acid and diamine oxidase (DAO) in blood, improving intestinal functions and preventing inflammatory intestinal disease.

4. The food of claim 1, wherein, the food is effective at improving metabolism of five amino acids including branched-chain amino acids and aromatic amino acids, including leucine, isoleucine, valine, tyrosine and phenylalanine, significantly related to diabetes, and improving protein metabolism.

5. The food of claim 1, wherein, the food is effective at reducing intestinal permeability, inhibiting inflammatory response, boosting blood insulin, improving pancreatic function and protein metabolism, increasing blood insulin and preventing diabetes.

6. The food of claim 1, wherein, the food is effective at lowering low-density lipoprotein cholesterol and triglyceride, improving lipid metabolism and preventing cardiovascular and cerebrovascular diseases.

7. The food of claim 1, wherein, the food is effective at reducing uric acid, improving nucleic acid metabolism, preventing gout and improving renal function.

8. The food of claim 1, wherein, the food is effective at reducing blood lead.

9. The food of claim 1, wherein, the food is effective at reducing alanine aminotransferase, indirect bilirubin, total bilirubin, and improving liver function.

10. The food of claim 1, wherein, the food is effective at improving hematological parameters of hemoglobin content, mean hemoglobin content, mean hemoglobin concentration and globulin.

11. The food of claim 1, wherein, the food is effective at improving albumin, albumin/globulin ratio (AIG) and immunoglobulin IgA and enhancing immunocompetence.

12. A medicament, consisting of an anti-inflammatory combination, wherein,
the anti-inflammatory combination consists of: a functional oligosaccharide and a common oligosaccharide, the functional oligosaccharide is a combination of an inulin and a galacto-oligosaccharide, and the common oligosaccharide is a combination of a polydextrose and a water-insoluble dietary fiber for providing a microbial reproductive environment;
a weight ratio of the inulin, the galacto-oligosaccharide, the polydextrose and the water-insoluble dietary fiber is (10-30): (5-30): (10-40): (10-50).

13. The medicament of claim 12, wherein, the medicament is effective at inhibiting inflammatory responses, and the anti-inflammatory combination reduces an inflammatory cytokine selected from the group consisting of interleukin-12p70 (IL-12p70), interleukin-13 (IL-13), interleukin-2 (IL-2), interleukin-23 (IL-23) and cytokine RANTES (regulated upon activation, normal T cell expressed and secreted), and increases an anti-inflammatory cytokine selected from the group consisting of interleukin-1 receptor antagonist (IL-1RA) and interleukin-4 (IL-4).

14. The medicament of claim 12, wherein, the medicament is effective at improving a utilization rate of glutamine, reducing intestinal permeability targeting marker including D-lactic acid and diamine oxidase (DAO) in blood, improving intestinal functions and preventing inflammatory intestinal disease.

15. The medicament of claim 12, wherein, the medicament is effective at improving metabolism of five amino acids including branched-chain amino acids and aromatic amino acids, including leucine, isoleucine, valine, tyrosine and phenylalanine, significantly related to diabetes, and improving protein metabolism.

16. The medicament of claim 12, wherein, the medicament is effective at reducing intestinal permeability, inhibiting inflammatory response, boosting blood insulin, improving pancreatic function and protein metabolism, increasing blood insulin and preventing diabetes.

17. The medicament of claim 12, wherein, the medicament is effective at lowering low-density lipoprotein cholesterol and triglyceride, improving lipid metabolism and preventing cardiovascular and cerebrovascular diseases.

18. The medicament of claim 12, wherein, the medicament is effective at reducing uric acid, improving nucleic acid metabolism, preventing gout and improving renal function.

19. The medicament of claim 12, wherein, the medicament is effective at reducing blood lead.

20. The medicament of claim 12, wherein, the medicament is effective at reducing alanine aminotransferase, indirect bilirubin, total bilirubin, and improving liver function.

21. The medicament of claim 12, wherein, the medicament is effective at improving hematological parameters of hemoglobin content, mean hemoglobin content, mean hemoglobin concentration and globulin.

22. The medicament of claim 12, wherein, the medicament is effective at improving albumin, albumin/globulin ratio (A/G) and immunoglobulin IgA for improving immunocompetence.

* * * * *